United States Patent
Schwarz et al.

(10) Patent No.: US 12,127,928 B2
(45) Date of Patent: Oct. 29, 2024

(54) COMPOSITE IMPLANT

(71) Applicant: Medical 21, Inc., Plymouth, MN (US)

(72) Inventors: Chaid D. Schwarz, Medina, MN (US); Eric E. Solien, Lino Lakes, MN (US); Jeff R. Vreeman, Brooklyn Park, MN (US); Manuel A. Villafana, Wayzata, MN (US)

(73) Assignee: Medical 21, Inc., Plymouth, MN (US)

( * ) Notice: Subject to any disclaimer, the term of this patent is extended or adjusted under 35 U.S.C. 154(b) by 0 days.

(21) Appl. No.: 18/531,315

(22) Filed: Dec. 6, 2023

(65) Prior Publication Data

US 2024/0180687 A1    Jun. 6, 2024

Related U.S. Application Data

(60) Provisional application No. 63/430,538, filed on Dec. 6, 2022.

(51) Int. Cl.
   *A61F 2/06*   (2013.01)
   *A61F 2/07*   (2013.01)

(52) U.S. Cl.
   CPC .............. *A61F 2/062* (2013.01); *A61F 2/06* (2013.01); *A61F 2/07* (2013.01); *A61F 2210/0004* (2013.01); *A61F 2230/0069* (2013.01)

(58) Field of Classification Search
   CPC .... A61F 2/04; A61F 2/06; A61F 2/062; A61F 2/07; A61F 2002/072; A61F 2210/0004;
   (Continued)

(56) References Cited

U.S. PATENT DOCUMENTS

| 7,998,188 B2 | 8/2011 | Zilla et al. |
| 8,017,396 B2 | 9/2011 | Kumar |

(Continued)

FOREIGN PATENT DOCUMENTS

| CN | 112156229 A | 1/2021 |
| CZ | 306213 B6 | 10/2016 |

(Continued)

OTHER PUBLICATIONS

"PREVENT IV Investigators*. Efficacy and Safety of Edifoligide, an E2F Transcription Factor Decoy, for Prevention of Vein Graft Failure Following Coronary Artery Bypass Graft Surgery.", JAMA. 2005;294(19):2446. doi:10.1001/jama.294.19.2446.

(Continued)

*Primary Examiner* — Dinah Baria
(74) *Attorney, Agent, or Firm* — Billion & Armitage

(57) ABSTRACT

A composite implant having multiple open-pore biodegradable polymer layers mechanically supported by a permanent structure positioned between adjacent polymer layers drives a native response for cellular infiltration, which facilitates progressive cellular-driven remodeling, cellular organization, and native extra-cellular matrix (ECM) deposition. This leads to endogenous tissue remodeling of the implant over time. The support structure provides mechanical support to the implant to effectively carry impressed mechanical load while the remodeling process is ongoing. The polymer layers are formulated to fully degrade over time, leaving only the new native tissue supported by the permanent support structure.

16 Claims, 30 Drawing Sheets

(58) Field of Classification Search
CPC ...... A61F 2250/0028; A61F 2250/0023; A61F 2230/0069; B32B 5/02; B32B 5/26; B32B 2250/03; B32B 2535/00
See application file for complete search history.

(56) References Cited

U.S. PATENT DOCUMENTS

| | | | |
|---|---|---|---|
| 8,172,746 | B2 | 5/2012 | Zilla et al. |
| 9,683,216 | B2* | 6/2017 | Shin ................. A61F 2/062 |
| 10,954,540 | B2 | 3/2021 | Schwarz et al. |
| 2007/0293932 | A1* | 12/2007 | Zilla ................. A61F 2/856 623/1.53 |
| 2008/0161839 | A1 | 7/2008 | Shalev |
| 2014/0257462 | A1 | 9/2014 | Orion et al. |
| 2014/0332121 | A1 | 11/2014 | Park et al. |
| 2015/0086607 | A1* | 3/2015 | Johnson ............ A61L 27/3804 623/1.13 |
| 2017/0319325 | A1* | 11/2017 | La Francesca ....... C12M 25/14 |
| 2018/0214611 | A1 | 8/2018 | Serino et al. |
| 2023/0363881 | A1* | 11/2023 | Zhu .................... A61F 2/82 |

FOREIGN PATENT DOCUMENTS

| | | |
|---|---|---|
| KR | 20220059391 A | 5/2022 |
| WO | 2012109309 A3 | 11/2012 |
| WO | 2014007631 A1 | 1/2014 |
| WO | 2015008152 A3 | 5/2015 |
| WO | 2015194950 A1 | 12/2015 |
| WO | 2016120456 A1 | 8/2016 |
| WO | 2017055926 A1 | 4/2017 |
| WO | 2017072229 A1 | 5/2017 |
| WO | 2019129640 A1 | 7/2019 |
| WO | 2019237014 A1 | 12/2019 |
| WO | 2020156711 A1 | 8/2020 |
| WO | 2020182863 A1 | 9/2020 |
| WO | 2021170595 A1 | 9/2021 |
| WO | 2022101370 A1 | 5/2022 |

OTHER PUBLICATIONS

Ambrosetti, M, et al., "Deep Vein Thrombosis among Patients Entering Cardiac Rehabilitation after Coronary Artery Bypass Surgery", Chest. 2004;125(1):191-196. doi:10.1378/chest.125.1.191.
Berger, K., et al., "Healing of Arterial Prostheses in Man", Ann Surg. 1972;175(1):118-127. doi:10.1097/00000658-197201000-00018.
Bottaro, Larsen, B., "Current advances in research and clinical applications of PLGA-based nanotechnology", Bone. 2008;23(1):1-7. doi:10.1586/erm.09.15.Current.
Chaparro, FJ, et al., "Biomimetic microstructural reorganization during suture retention strength evaluation of electrospun vascular scaffolds", J Biomed Mater Res—Part B Appl Biomater. 2016;104(8):1525-1534. doi:10.1002/jbmb.33493.
Chung, L, et al., "Key players in the immune response to biomaterial scaffolds for regenerative medicine", Adv Drug Deliv Rev. 2017;114:184-192. doi:10.1016/j.addr.2017.07.006.
Dacey, LJ, et al., "Long-term outcomes of endoscopic vein harvesting after coronary artery bypass grafting", Circulation. 2011;123(2):147-153. doi:10.1161/CIRCULATIONAHA.110.960765.
De Vries, MR, et al., "Vein graft failure: From pathophysiology to clinical outcomes", Nat Rev Cardiol. 2016;13 (8):451-470. doi:10.1038/nrcardio.2016.76.
Deppe, AC, et al., "Endoscopic vein harvesting for coronary artery bypass grafting: A systematic review with meta-analysis of 27,789 patients", J Surg Res. 2013;180(1):114-124. doi:10.1016/j.jss.2012.11.013.
Desai, M, et al., "Role of prosthetic conduits in coronary artery bypass grafting", Eur J Cardio-thoracic Surg. 2011;40 (2):394-398. doi:10.1016/j.ejcts.2010.11.050.

Dziki, JL, et al., "Extracellular Matrix Bioscaffolds as Immunomodulatory Biomaterials", Tissue Eng—Part A. 2017;23 (19-20):1152-1159. doi:10.1089/ten.tea.2016.0538.
Garg, K., et al., "Macrophage functional polarization (M1/M2) in response to varying fiber and pore dimensions of electrospun scaffolds", Biomaterials. 2013;34(18):4439-4451. doi:10.1016/j.biomaterials.2013.02.065.
Godwin, JW, et al., "Chasing the recipe for a pro-regenerative immune system", Semin Cell Dev Biol. 2017;61:71-79. doi:10.1016/j.semcdb.2016.08.008.
Gupta, P., et al., "Bioresorbable silk grafts for small diameter vascular tissue engineering applications: In vitro and in vivo functional analysis", Acta Biomater. 2020;105:146-158. doi:10.1016/j.actbio.2020.01.020.
Harskamp, RE, et al., "Vein graft preservation solutions, patency, and outcomes after coronary artery bypass graft surgery: Follow-up from PREVENT IV randomized clinical trail", JAMA Surg. 2014;149(8):798-805 doi:10.1001/jamasurg.2014.87.
Hasan, A., et al., "Electrospun scaffolds for tissue engineering of vascular grafts", Acta Biomater. 2014;10(1):11-25. doi:10.1016/j.actbio.2013.08.022.
Head, SJ, et al., "Current practice of state-of-the-art surgical coronary revascularization", Circulation. 2017;136 (14):1331-1345. doi:10.1161/CIRCULATIONAHA.116.022572.
Hess, CN, et al., "Saphenous vein graft failure after coronary artery bypass surgery insights from PREVENT IV", Circulation. 2014;130(17):1445-1451. doi:10.1161/CIRCULATIONAHA.113.008193.
Illig, KA, et al., "Financial impact of endoscopic vein harvest for infrainguinal bypass", J Vasc Surg. 2003;37 (2):323-330. doi:10.1067/mva.2003.2.
Isaka, M., et al., "Experimental study on stability of a high-porosity expanded polytetrafluoroethylene graft in dogs", Ann Thorac Cardiovasc Surg. 2006;12(1):37-41.
Knight, DK, "Vascular grafting strategies in coronary intervention", Front Mater. 2014;1(June):1-16. doi:10.3389/fmats.2014.00004.
Konstantinov, IE, et al., "The surgeon who performed the first successful clinical coronary artery bypass operation", Ann Thorac Surg. 2000;69(6):1966-1972. doi:10.1016/S0003-4975(00)01264-9.
Landes, CA, et al., "In-patient versus in vitro degradation of P(L/DL)LA and PLGA", J Biomed Mater Res—Part B Appl Biomater. 2006;76(2):403-411. doi:10.1002/jbm.b.30388.
Madden, LR, et al., "Proangiogenic scaffolds as functional templates for cardiac tissue engineering", Proc Natl Acad Sci U S A. 2010;107(34):15211-15216. doi:10.1073/pnas.1006442107.
Matsuzaki, Y, et al., "The evolution of tissue engineered vascular graft technologies: From preclinical trials to advancing patient care", Appl Sci. 2019;9(7). doi:10.3390/app9071274.
Mehta, RI, et al., "Pathology of explanted polytetrafluoroethylene vascular grafts", Cardiovasc Pathol. 2011;20 (4):213-221. doi:10.1016/j.carpath.2010.06.005.
Melly, L, et al., "Fifty years of coronary artery bypass grafting", J Thorac Dis. 2018; 10(3):1960-1967. doi:10.21037/jtd.2018.02.43.
Paletta, CE, et al., "Major leg wound complications after saphenous vein harvest for coronary revascularization", Ann Thorac Surg. 2000;70(2):492-497. doi:10.1016/S0003-4975(00)01414-4.
Park, K, et al., "Injectable, long-acting PLGA formulations: Analyzing PLGA and understanding microparticle formation", J Control Release. 2019;304:125-134. doi:10.1016/j.jconrel.2019.05.003.
Peck, M, et al., "The evolution of vascular tissue engineering and current state of the art", Cells Tissues Organs. 2011;195(1-2):144-158. doi:10.1159/000331406.
Radke, D, et al., "Tissue Engineering at the Blood-Contacting Surface: A Review of Challenges and Strategies in Vascular Graft Development", Adv Healthc Mater. 2018;7(15):1-24. doi:10.1002/adhm.201701461.
Rousselle, SD, et al., "Pathology of Bioabsorbable Implants in Preclinical Studies", Toxicol Pathol. 2019;47 (3):358-378. doi:10.1177/0192623318816681.
Samano, N, et al., "The no-touch saphenous vein for coronary artery bypass grafting maintains a patency, after 16 years, compa-

(56) References Cited

OTHER PUBLICATIONS rable to the left internal thoracic artery: A randomized trial", J Thorac Cardiovasc Surg. 2015;150 (4):880-888. doi:10.1016/j.jtcvs.2015.07.027.

Sussman, EM, et al., "Porous implants modulate healing and induce shifts in local macrophage polarization in the foreign body reaction", Ann Biomed Eng. 2014;42(7):1508-1516. doi:10.1007/s10439-013-0933-0.

Tu, Z, et al., "Design of therapeutic biomaterials to control inflammation", Nat Rev Mater. 2022;0123456789. doi:10.1038/s41578-022-00426-z.

Veiseh, et al., "Size- and shape-dependent foreign body immune response to materials implanted in rodents and non-human primates", Nature Mater 14, 643-651 (2015). https://doi.org/10.1038/nmat4290.

Wang, Z, et al., "The effect of thick fibers and large pores of electrospun poly(ε-caprolactone) vascular grafts on macrophage polarization and arterial regeneration", Biomaterials. 2014;35(22):5700-5710.

Wissing, TB, et al., "Biomaterial-driven in situ cardiovascular tissue engineering—a multi-disciplinary perspective", npj Regen Med. 2017;2(1):1-19. doi:10.1038/s41536-017-0023-2.

Woodard, LN, et al., "Hydrolytic Degradation and Erosion of Polyester Biomaterials", ACS Macro Lett. 2018;7 (8):976-982. doi:10.1021/acsmacrolett.8b00424.

Zilla, P, et al., "Prosthetic vascular grafts: Wrong models, wrong questions and no healing. Biomaterials", 2007;28 (34):5009-5027. doi:10.1016/j.biomaterials.2007.07.017.

"Invitation to Pay Additional Fees and, Where Applicable, Protest Fee Mailed on Mar. 14, 2024", 16 Pages.

* cited by examiner

COMPOSITE IMPLANT

CROSS-REFERENCE TO RELATED APPLICATIONS

This application claims the benefit of priority to U.S. Provisional Patent Application Ser. No. 63/430,538, filed on Dec. 6, 2022, and entitled "Composite Implant", the content of which being incorporated herein in its entirety.

FIELD OF THE INVENTION

The present invention relates to composite implants generally, and more particularly to implantable constructs that are naturally remodelable in vivo to promote the creation of native tissue structures that replace a portion of the implantable constructs and serve as functional tissue replacements or alternatives.

BACKGROUND OF THE INVENTION

Ischemic heart disease is the leading cause of morbidity and mortality in the world. The most common type of heart disease is coronary artery disease in which the arteries that feed blood to the heart become blocked by atherosclerosis. To resolve and generate adequate reperfusion, autologous vessels such as veins and arteries are harvested and used to bypass blocked coronary arteries. With nearly 800,000 bypass surgeries each year, approximately 80% of worldwide procedures are completed by harvesting the saphenous vein. Although recent outcomes are improving with advanced techniques, nearly 30% of saphenous vein grafts fail within 12-18 months of the bypass procedure, and nearly 50% of saphenous vein grafts fail in the first 10 years. Vein graft failure is complex owing to factors such as pathophysiological mechanisms of the native vessels (intimal hyperplasia, atherosclerosis, or the rupture of plaques), blood flow dynamics, surgical processing, implant techniques, and patient medical history. In addition to the complexity of the open heart procedure, harvesting of the autologous vessels is associated with peripheral pain, infection, rehabilitation, and significant costs.

In addition, the demand for autologous vessels in bypass procedures greatly exceeds availability. When autologous vessels are not available for grafting, synthetic grafts are sometimes used for large-diameter vessels. However, viable synthetic small diameter (<6 mm) conduits for coronary artery bypass grafts remain elusive due to various failure modes such as thrombogenicity, cell-driven hyperplasia, and immune-mediated foreign body reaction.

The procedure of coronary artery bypass grafting (CABG) has spanned several decades of development with influences from many pioneers. Significant technical advances were seen in the 1960s, beginning with the first CABG procedure in 1961 by Robert Goetz. Soon thereafter, David Sabiston completed the first hand-sewn CABG by anastomosing the saphenous vein graft (SVG) to the right coronary artery. Various autologous vessels have been investigated for CABG, including the SVG, the cephalic vein, the left and right internal thoracic arteries, the radial artery, and the right gastroepiploic artery. The standard today remains bypassing the left ascending coronary artery using the left internal thoracic artery while SVG's are used to bypass other diseased coronary artery targets. Aside from failure rates of these conduits, use of autologous vessels involves removing existing blood pathways for the patient. In each case, there are risks associated with the removal and use of these vessels for these procedures, including deep vein thrombosis, and bleeding, swelling, pain, and infection at the removal site.

Efforts have been undertaken to develop synthetic vascular grafts in the fields of non-degradable synthetic conduits, biodegradable constructs, and tissue-engineered biologic vascular grafts. Attempts to manufacture synthetic vascular grafts were initially attempted with non-degradable materials such as polytetrafluoroethylene (PTFE), polyether terephthalate (PET), and more recently polyurethane. Conduits manufactured from these materials are mechanically strong, easily sutured in place, and capable of withstanding very high radial pressures. Although Dacron and PTFE polymers have been successfully utilized as large diameter prostheses, they have not been clinically successful in small diameter (<6 mm) applications due to risk of thrombosis, calcification, hyperplasia, and foreign body reaction. Historical evidence suggests that non-degradable conduits have limited neointima development, and that limited porosity of such materials likewise limits transmural cellular ingrowth, which excludes the possibility for native remodeling.

As a result of the limitations associated with the biostable polymers described above, extensive research has focused on engineered constructs with biodegradable polymers. Certain synthetic and natural polymers are prone to chemical modification upon exposure to physiological conditions, including exposure to blood at physiological conditions. Examples of such polymers include poly(lactic acid) (PLA), polydioxanone (PDO), polycaprolactone (PCL), poly(glycerol sebacate) (PGS), and natural polymers like fibrin, collagen, elastin, cellulose, chitosan, and hyaluronic acid. Due to the nature of degradation of such polymers, constructs are designed to degrade in vivo over time, and to perform as temporary scaffolds until native tissue remodeling is sufficient to perform the necessary tasks. In some examples, the temporary scaffolds are designed to control blood flow by mitigating hemorrhage until sufficient native tissue remodeling forms neointimal sealing layers and mechanically supports the graft. As a biodegradable construct, a primary challenge is balancing mechanical loss while promoting the remodeling process. This exchange is highly time dependent. If the construct mechanically weakens too quickly, anastomotic suture failure, graft aneurysm, or transmural hemorrhage can occur. Some biodegradable materials exhibit rapid mechanical degradation over a period of weeks, while others degrade much more slowly over a period of years.

Singular and even composite biodegradable polymer constructs have previously failed to achieve a successful permanent implant, due to a lack of implant mechanics, premature loss of mechanical strength prior to remodeling, poor blood compatibility, and occlusive hyperplasia.

It is therefore an object of the present invention to provide an implantable construct that overcomes the shortcomings of conventional devices. The implantable construct may comprise a synthetic bypass graft for the treatment of ischemic heart disease, and may particularly comprise a synthetic construct formed as tubular body.

It is another object of the present invention to provide a permanently implantable tubular device as a fluid conduit. The implantable fluid conduit may comprise an in situ tissue engineered construct that is capable of handling physiological mechanical loads while inducing native regenerative healing processes that functionally drive host cellular response to the material and microenvironment of the construct. The permanently implanted construct preferably achieves a state of homeostasis.

It is a further object of the present invention to provide a surgical alternative to angioplasty, coronary artery stenting, and traditional coronary artery bypass grafting for restoring blood perfusion. The surgical alternative utilizes a synthetic composite implant that does not exhibit the drawbacks of conventional synthetic grafts.

SUMMARY OF THE INVENTION

By means of the present invention, native tissue structures can be generated through progressive remodeling of a composite biodegradable implant. The implant may be a refined combination of distinct layers that generates post-operative stability to the newly forming tissues. The layers include fibrous open-pore biodegradable polymer arrangements that are mechanically supported by a permanent support structure positioned between adjacent polymer layers and exhibiting radial compliance properties. The unique morphology of the fibrous biodegradable polymer layers primes the native response for unencumbered cellular infiltration, which facilitates progressive cellular-driven remodeling, cellular organization, and native extra-cellular matrix (ECM) deposition leading to endogenous tissue regeneration of the implant over time. To limit adverse host immune response, the implant is designed with biodegradable polymers having targeted degradation rates that are relevant to the progressive cellular infiltration and cell-driven remodeling.

The composite implant, in some embodiments, may be formed as a stand-alone product for use as a synthetic acellular surgically implanted blood vessel. The implant interacts exceptionally well with blood to limit thrombosis, platelet aggregation, and blood complement activation. Mechanical and biomimetic characteristics may be tuned to generate inherent mechanical integrity and biologically relevant flexibility at implant. In this embodiment, the support structure provides radial support to effectively carry cyclic blood pressure loading while minimizing risk of aneurysm formation. The polymer layers of the composite graft effectively seal blood within the lumen of the vessel, and influences formation of a neointimal layer that transitions the fibro-cellular network into oriented cellular tissue-promoting endothelization. The polymer layers are formulated to fully degrade over time, leaving only the new native tissue, supported by the permanent support structure, in its place.

In one embodiment, the composite implant includes a radially compliant resilient tubular support disposed between porous biodegradable polymer layers, with the support defining an axis and having a structure defining a tubular wall with openings in the wall of sufficient size to permit migration of human cells therethrough, the structure being capable of resilient radial compliance suitable to promote cellular remodeling of the composite implant into a vessel of autologous tissue reinforced by the support. The biodegradable polymer layers may be formed as non-woven arrangements of polymer fibers.

In some embodiments, the support includes a knit arrangement of spaced apart elements, which may be made of metal. The support may be embedded between the biodegradable polymer layers to form a tube-shaped composite implant.

At least one of the biodegradable polymer layers may experience a loss of at least 50% of mechanical strength in no less than 30 days of continuous exposure to human blood at physiological conditions. In some embodiments, each of the biodegradable polymer layers may experience a loss of at least 50% of mechanical strength in no less than 30 days of continuous exposure to human blood at physiological conditions. In some embodiments, at least one of the biodegradable polymer layers may experience a loss of at least 90% of mechanical strength in no less than 30 days of continuous exposure to human blood at physiological conditions. In some embodiments, at least one of the biodegradable polymer layers may experience a loss of at least 90% of mechanical strength in no less than 90 days of continuous exposure to human blood at physiological conditions. In some embodiments, at least one of the biodegradable polymer layers may experience a loss of at least 90% of mechanical strength in no less than 180 days of continuous exposure to human blood at physiological conditions. In some embodiments, at least one of the biodegradable polymer layers experiences loss of mechanical strength at a different rate than another of the biodegradable polymer layers.

The biodegradable polymer fibers may comprise one or more of polylactic acid, polyglycolic acid, copolymers of polylactic acid and polyglycolic acid such as poly(lactic-co-glycolide), poly(glycerol sebacate), degradable polyurethanes, polycaprolactone, polyethylene glycol, polydioxanone, elastin-like polymers, copolymers with trimethylene carbonate, and derivatives of such polymers.

In another embodiment, a composite implant includes an inner layer, a second layer positioned adjacent to the first layer, an outer layer arranged with the second layer between the inner layer and the outer layer, and a resilient support between the inner layer and the outer layer, wherein the support defines openings between adjacent spaced apart elements. The inner layer may include a first non-woven arrangement of biodegradable polymer fibers having an average fiber diameter of less than 1 µm. The second layer may include a second arrangement of biodegradable polymer fibers having an average fiber diameter of between 1 and 20 µm. The outer layer may include a third arrangement of biodegradable polymer fibers having an average fiber diameter of between 1 and 20 µm.

In some embodiments, the second and third arrangements of biodegradable polymer fibers are non-woven. The inner layer may have a first thickness of between 1-200 µm, the second layer may have a thickness of between 50-500 µm, and the third layer may have a thickness of between 10-300 µm. Each of the inner layer, the second layer, and the outer layer may have a planimetric porosity of between 25-50%.

The composite implant of this embodiment may be substantially tubular with a defined lumenal axis. In some embodiments, the first non-woven arrangement of biodegradable polymer fibers is random, and at least one of the second and third non-woven arrangements of biodegradable fibers are one of: (i) aligned substantially parallel with the lumenal axis, or (ii) aligned substantially orthogonal to the lumenal axis. Each of the second and third non-woven arrangements of biodegradable polymer fibers may be one of: (i) aligned substantially parallel with the lumenal axis, or (ii) aligned substantially orthogonal to the lumenal axis. In other embodiments, each of the first, second, and third arrangements of biodegradable polymer fibers is random.

In some embodiments, the resilient support is tubular and radially compliant. The support may exhibit a radial compliance to promote smooth muscle cell organization as a component of cellular remodeling of the composite implant into a vessel of autologous tissue reinforced by the resilient support. In some embodiments, the resilient support includes knitted elements.

The composite implant may be formed as a tubular graft, wherein the inner layer forms a lumen along the lumenal axis, and wherein the lumen has a diameter of less than 6 mm.

The resilient support may be disposed between the second layer and the outer layer, and the second layer may be bonded to the outer layer. Moreover, the second layer may be bonded to the inner layer.

Another embodiment of a composite implant forms a tubular vascular graft that defines a lumenal axis, and includes a resilient tubular support exhibiting radial compliance with respect to the lumenal axis. The support may be disposed circumaxially between an inner biodegradable polymer layer and an outer biodegradable polymer layer. The inner layer may form a lumenal wall of the tubular vascular graft, and may include a first non-woven arrangement of biodegradable polymer fibers. The outer layer may include a second non-woven arrangement of biodegradable polymer fibers. At least one of the first and second non-woven arrangements may form a plurality of axially spaced apart circumferential recesses defining respective hinge regions at which at least one of the respective inner and outer layers are more flexible than non-hinge regions thereof.

At least some of the circumferential recesses may be arranged substantially perpendicularly to the lumenal axis. In this or other embodiments, at least some of the circumferential recesses are arranged non-perpendicularly with respect to the lumenal axis.

The circumferential recesses may be formed only in the inner layer.

The hinge regions may each include a vertex at which flexing of the respective inner or outer layer is focused.

The resilient tubular support may include knit elements, wherein the knit elements may include metal.

The composite implant may include an intermediate layer positioned adjacent to the inner layer, wherein the intermediate layer includes a third non-woven arrangement of biodegradable polymer fibers. The resilient tubular support may be embedded circumaxially between the intermediate layer and the outer layer. In some embodiments, the intermediate layer may be bonded to the outer layer. In some embodiments, the intermediate layer may be bonded to the inner layer.

A composite implant, comprising:
a radially compliant resilient tubular support disposed between porous biodegradable polymer layers, the support defining an axis and comprising a structure defining a tubular wall with openings in the wall of sufficient size to permit migration of human cells therethrough, the structure being capable of resilient radial compliance suitable to promote cellular remodeling of the composite implant into a vessel of autologous tissue reinforced by the support, and wherein the biodegradable polymer layers are formed as non-woven arrangements of polymer fibers.

The composite implant wherein the support comprises a knit arrangement of spaced apart elements.

The composite implant wherein the elements comprise metal.

The composite implant wherein the support is embedded between the biodegradable polymer layers to form a tube-shaped composite implant.

The composite implant wherein at least one of the biodegradable polymer layers experience loss of at least 50% of mechanical strength in no less than 30 days of continuous exposure to human blood at physiological conditions.

The composite implant wherein at least one of the biodegradable polymer layers experience loss of at least 90% of mechanical strength in no less than 90 days of continuous exposure to human blood at physiological conditions.

The composite implant wherein at least one of the biodegradable polymer layers experience loss of at least 90% of mechanical strength in no less than 180 days of continuous exposure to human blood at physiological conditions.

The composite implant wherein at least one of the biodegradable polymer layers experience loss of mechanical strength at a different rate than another of the biodegradable polymer layers.

The composite implant wherein the biodegradable polymer fibers comprise one or more of polylactic acid, polyglycolic acid, copolymers of polylactic acid and polyglycolic acid, poly(glycerol sebacate), degradable polyurethanes, polycaprolactone, polyethylene glycol, polydioxanone, elastin-like polymers, copolymers with trimethylene carbonate, and derivatives and copolymers thereof.

The composite implant formed as a vascular graft.

A composite implant, comprising:
an inner layer comprising a first non-woven arrangement of biodegradable polymer fibers having an average fiber diameter of less than 1 μm;
a second layer positioned adjacent to the first layer and comprising a second arrangement of biodegradable polymer fibers having an average fiber diameter of between 1 and 20 μm;
an outer layer arranged with the second layer between the inner layer and the outer layer, wherein the outer layer comprises a third arrangement of biodegradable polymer fibers having an average fiber diameter of between 1 and 20 μm; and
a resilient support between the inner layer and the outer layer, the support defining openings between adjacent spaced apart elements.

The composite implant wherein the second and third arrangements of biodegradable polymer fibers are non-woven.

The composite implant wherein the inner layer has a first thickness of between 1-200 μm, the second layer has a second thickness of between 50-500 μm, and the outer layer has a third thickness of between 10-300 μm.

The composite implant wherein each of the inner layer, the second layer, and the outer layer have a planametric porosity of between 25-50%.

The composite implant wherein the biodegradable polymer fibers include at least one of polylactic acid, polyglycolic acid, copolymers of polylactic acid and polyglycolic acid, poly(glycerol sebacate), degradable polyurethanes, polycaprolactone, polyethylene glycol, polydioxanone, elastin-like polymers, copolymers with trimethylene carbonate, and derivatives and copolymers thereof.

The composite implant being substantially tubular and defining a lumenal axis.

The composite implant wherein the first non-woven arrangement of biodegradable polymer fibers is random, and at least one of the second and third non-woven arrangements of biodegradable fibers are one of: (i) aligned substantially parallel with the lumenal axis; or (ii) aligned substantially orthogonal to the lumenal axis.

The composite implant wherein each of the second and third non-woven arrangements of biodegradable polymer fibers are one of: (i) aligned substantially parallel with the lumenal axis; or (ii) aligned substantially orthogonal to the lumenal axis.

The composite implant wherein each of the first, second, and third arrangements of biodegradable polymer fibers is random.

The composite implant wherein the resilient support is tubular and radially compliant.

The composite implant wherein the resilient support exhibits a radial compliance to promote smooth muscle cell organization as a component of cellular remodeling of the composite implant into a vessel of autologous tissue reinforced by the resilient support.

The composite implant wherein the resilient support includes a circular weft knit of the members.

The composite implant forming a tubular graft.

The composite implant wherein the inner layer forms a lumen along the lumenal axis, and wherein the lumen has a diameter of less than 6 mm.

The composite implant wherein the resilient support is disposed between the second layer and the outer layer, and the second layer is bonded to the outer layer.

The composite implant wherein each of the biodegradable polymer layers experience loss of at least 50% of mechanical strength in no less than 30 days of continuous exposure to human blood at physiological conditions.

A composite implant forming a tubular vascular graft defining a lumenal axis, the composite implant comprising:
  a resilient tubular support exhibiting radial compliance with respect to the lumenal axis, and being disposed circumaxially between an inner biodegradable polymer layer and an outer biodegradable polymer layer, the inner layer forming a lumenal wall of the tubular vascular graft and comprising a first non-woven arrangement of biodegradable polymer fibers, the outer layer comprising a second non-woven arrangement of biodegradable polymer fibers, at least one of the first and second non-woven arrangements forming a plurality of axially spaced apart circumferential recesses defining respective hinge regions at which at least one of the respective inner and outer layers are more flexible than non-hinge regions thereof.

The composite implant wherein at least some of the circumferential recesses are arranged substantially perpendicularly to the lumenal axis.

The composite implant wherein the circumferential recesses are axially spaced apart by between 0.1-5 mm.

The composite implant wherein at least some of the circumferential recesses are arranged non-perpendicularly with respect to the lumenal axis.

The composite implant wherein the circumferential recesses are formed only in the inner layer.

The composite implant wherein the hinge regions each include a vertex at which flexing of the respective inner or outer layer is focused.

The composite implant wherein the resilient tubular support comprises knit elements.

The composite implant wherein the elements comprise metal.

The composite implant, including an intermediate layer positioned adjacent to the inner layer and comprising a third non-woven arrangement of biodegradable polymer fibers.

The composite implant wherein the intermediate layer and the inner layer include the circumferential recesses.

The composite implant wherein the outer layer is free from the circumferential recesses.

The composite implant wherein the resilient tubular support is embedded circumaxially between the intermediate layer and the outer layer.

The composite implant wherein the intermediate layer is bonded to the outer layer.

The composite implant wherein the biodegradable polymer fibers comprise one or more of polylactic acid, polyglycolic acid, copolymers of polylactic acid and polyglycolic acid, poly(glycerol sebacate), degradable polyurethanes, polycaprolactone, polyethylene glycol, polydioxanone, elastin-like polymers, copolymers with trimethylene carbonate, and derivatives and copolymers thereof.

The composite implant wherein each of the biodegradable polymer layers experience loss of at least 50% of mechanical strength not less than 30 days subsequent to continuous exposure to human blood at physiological conditions.

A composite implant, comprising:
  a tubular inner layer defining a lumen, a lumenal axis, and a lumenal wall having a lumenal surface and an ablumenal surface, the inner layer comprising a first arrangement of biodegradable polymer fibers, wherein the first arrangement is effective to substantially prevent migration of human red blood cells through the lumenal wall;
  a second layer positioned circumferentially about and adjacent to the inner layer, and comprising a second arrangement of biodegradable polymer fibers defining a second porosity of interconnected pores that facilitates infiltration of human immune and progenitor cells into the second layer;
  an outer layer positioned so that at least a portion of the second layer is between the inner layer and the outer layer, wherein the outer layer comprises a third arrangement of biodegradable polymer fibers defining a third porosity of interconnected pores that facilitate infiltration of human immune and progenitor cells into the third layer; and
  a resilient support between the inner layer and the outer layer, the support defining openings between adjacent spaced apart elements.

The composite implant wherein the second layer is mechanically bonded to the ablumenal surface of the inner layer.

The composite implant wherein the second porosity of interconnected pores facilitate migration of the human immune and progenitor cells throughout the second layer, and the third porosity of interconnected pores facilitate migration of the human immune and progenitor cells throughout the third layer.

The composite implant wherein the second and third porosities of interconnected pores each have average pore sizes that do not restrict infiltration of human cells into and throughout the second and third layers.

The composite implant wherein the outer layer is mechanically bonded to the second layer through the openings in the resilient support.

The composite implant wherein at least one of the first, second, and third arrangements of biodegradable polymer fibers are non-woven.

The composite implant wherein each of the first, second, and third arrangements of biodegradable polymer fibers are non-woven.

The composite implant wherein the inner layer has a first thickness of between 1-200 μm, the second layer has a second thickness of between 50-500 μm, and the outer layer has a third thickness of between 10-300 μm.

The composite implant wherein the first arrangement of biodegradable polymer fibers is random, and at least one of the second and third arrangements of biodegradable polymer fibers are one of: (i) aligned substantially parallel with the lumenal axis; or (ii) aligned substantially orthogonal to the lumenal axis.

The composite implant wherein each of the second and third arrangements of biodegradable polymer fibers are one of: (i) aligned substantially parallel with the lumenal axis; or (ii) aligned substantially orthogonal to the lumenal axis.

The composite implant wherein each of the first, second, and third arrangements of biodegradable polymer fibers is random.

A composite implant forming a tubular vascular graft defining a lumenal axis, the composite implant comprising: a resilient tubular support exhibiting radial compliance with respect to the lumenal axis, and being disposed circumaxially between a first biodegradable polymer layer and a second biodegradable polymer layer, the first layer comprising a first non-woven arrangement of biodegradable polymer fibers, and the second layer comprising a second non-woven arrangement of biodegradable polymer fibers, wherein the tubular vascular graft exhibits an initial bending stiffness of less than 0.5 N/mm when evaluated according to an ISO 7198 test method.

The composite implant wherein the tubular vascular graft exhibits an initial bending stiffness of less than 0.2 N/mm when evaluated according to the ISO 7198 test method.

The composite implant wherein at least one of the first and second layers form a plurality of axially spaced apart circumferential recesses defining respective hinge regions.

The composite implant wherein at least one of the respective first and second layers are more flexible at the respective hinge regions than at non-hinge regions thereof.

The composite implant wherein at least some of the circumferential recesses are arranged non-perpendicularly with respect to the lumenal axis.

The composite implant, including a third layer positioned adjacent to the first layer and comprising a third non-woven arrangement of biodegradable polymer fibers.

The composite implant wherein the resilient tubular support is embedded circumaxially between the third layer and the second layer, and wherein the third layer is bonded to the second layer.

The composite implant wherein the circumferential recesses are formed only in the first and third layers.

DETAILED DESCRIPTION OF THE INVENTION

Figure 1:
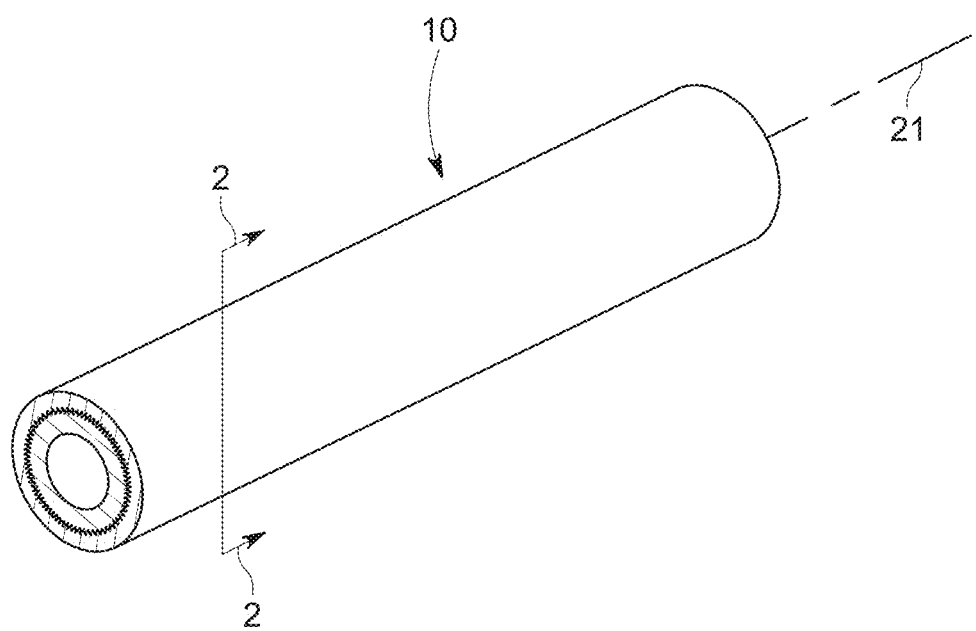
FIG. 1 is a schematic illustration of a composite implant of the present invention.

The objects and features enumerated above together with other objects, features, and advances represented by the present invention will now be presented in terms of detailed embodiments described with reference to the drawing figures. Other aspects of the invention are recognized as being with the grasp of those having ordinary skill in the art.

Spatially relative terms, such as "below", "above", "lower", "upper", and the like may be used to describe spatial relationships among elements as illustrated in the drawing figures. It is to be understood that the use of such terms is not intended to be limiting, and that such terms may encompass different orientations of the apparatus when in use, or generally in orientations other than that illustrated in the drawing figures.

Disclosed herein is a device for use as a permanently implanted, in-situ tissue engineered construct from a composite of biodegradable polymer and a reinforcing support. In some embodiments, the construct is designed for in situ tissue regeneration in the form of a vessel for use as a fluid conduit. The device preferably carries mechanical loading while inducing a regenerative healing process that functionally drives a host cellular response to the material and microenvironment of the implant. For the purposes of this disclosure, therefore, reference will be made to graft constructs that are configured to carry fluids such as blood or other body fluids from a first location to a second location. However, it is to be understood that other, non-vessel applications of the constructs described herein may be readily conceived of by those of ordinary skill in the art.

The composite graft of the present invention is designed to induce the migration of human immune and progenitor cells into the scaffold formed by one or more biodegradable polymer layers, such that an autologous tissue vessel is progressively formed by native remodeling mechanisms while the biodegradable polymer slowly degrades or bioabsorbs into the patient's body. The remodeling mechanism ultimately replaces the biodegradable polymer scaffold, leaving only the reinforcing support to permanently reinforce the new autologous tissue vessel. The composite grafts described herein may support host tissue remodeling solely through host-mediated regenerative processes that eventually result in a structure that exhibits mechanical properties suitable to support cardiovascular pressures, as well as long-term biocompatibility and patency.

For the purposes hereof, the term "scaffold" refers to the structure of the composite implant into which or upon which cells may migrate or attach. In some embodiments, the scaffold of the composite implant refers to the one or more layers of biodegradable polymer. In other embodiments, however, the scaffold of the composite implant may refer to the one or more layers of biodegradable polymer and the resilient support.

Figure 2:
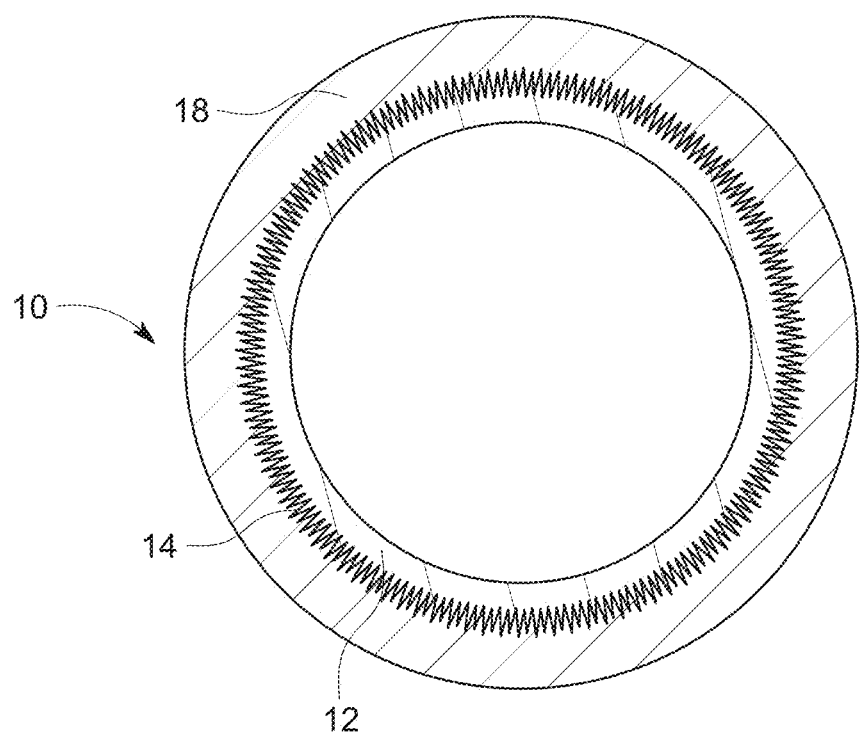
FIG. 2 is a cross-sectional view of the composite implant illustrated in FIG. 1, as taken along cut line 2-2.

One embodiment of the present invention is illustrated in FIG. 1, wherein composite implant 10 is formed as a tubular graft device, such as a vascular graft. As shown in the cross-sectional view of FIG. 2, taken along cut line 2-2 in FIG. 1, implant 10 includes a tubular support 12 disposed between an inner layer 14 and an outer layer 18. Inner and outer layers 14, 18 may comprise the same or different materials of construction, but each preferably comprise biocompatible materials. For the purposes hereof, the term "biocompatible" is intended to refer to a property that permits a material to benignly interact with the host, and without significant physiologically adverse effects when implanted within the host.

In some embodiments, one or more of the layers of implant 10, such as one or more of inner layer 14 and outer layer 18 may be constructed from one or more biocompatible polymer materials. Various biocompatible polymer materials are known for use in implants, and it is contemplated that various polymer materials may be utilized in constructions of the present invention in order to provide suitable characteristics to implant 10. Example biocompatible but non-bioabsorbable polymer materials that are known for use in implantable devices include polytetrafluoroethylene (PTFE), expanded polytetrafluoroethylene (e-PTFE), polyurethanes, polypropylene, polyethylene terephthalate (PET), polyaryletherketone, silicone, and the like. In some embodiments, biodegradable polymer materials may be utilized in the construction of the composite implants of the present invention, including in the construction of inner and outer layers 14, 18 of composite implant 10.

In some embodiments, the polymer scaffold of the composite implant of the present invention, including inner and outer layers 14, 18 of composite implant 10 is biodegradable. For the purposes hereof, the term "biodegradable" is intended to refer to a material that degrades within a human body within a discernable period of time, such as days, weeks, or years. Biodegradation involves a process in which the material decomposes by chemical degradation over time. Example chemical degradation routes include hydrolytic degradation, oxidation degradation, and enzymatic degradation. Biodegradable materials include bioabsorbable and biofragmentable materials. Example biodegradable polymer materials include polylactic acid (PLA), polyglycolic acid (PGA) copolymers of PLA and PGA such as poly(lactic-co-glycolide) (PLGA), poly(glycerol sebacate) (PGS), degradable polyurethanes, polycaprolactone (PCL), polyethylene glycol (PEG), polydioxanone (PDO), elastin-like polymers (ELP), copolymers such as PLA or PGA with trimethylene carbonate (TMC), and derivatives of these polymers.

In some embodiments, one or more of the polymer layers includes a PLGA polymer having a PLA/PGA ratio of between 50/50 to 95/5 (wt. %/wt. %). In some embodiments, one or more of the polymer layers includes a PLGA polymer having a PLA/PGA ratio of between 60/40 to 95/5 (wt. %/wt. %). In some embodiments, one or more of the polymer layers includes a PLGA polymer having a PLA/PGA ratio of between 75/25 to 95/5 (wt. %/wt. %). In some embodiments, one or more of the polymer layers includes a PLGA polymer having a PLA/PGA ratio of between 80/20 to 90/10 (wt. %/wt. %).

Other example polymer materials for the scaffold include biological materials such as collagen, fibrin, and elastin. Biological materials may be incorporated into one or more of the polymer layers, either as a component of the layer or a coating thereon, or may be contained within pores or other channels within the polymer layers comprising the scaffold.

Specific characteristics influence polymer degradation, including molecular structure, molecular weight, hydrophobicity, crystallinity, phase microstructure, and material processing. In the case of a plurality of layers in the scaffold, the layers, such as inner and outer layers 14, 18, may exhibit the same or different biodegradation rates. Additionally, one or more of the layers may include one or more sub-layers, such as a sub-layer with one type of biodegradable material, and another sub-layer with another type of biodegradable material, wherein the different types of biodegradable materials may exhibit similar or dissimilar biodegradation rates.

Biodegradation rates may be determined by various methods, such as loss of mass over time and loss of mechanical strength over time. Applicant has found that measuring biodegradation rate by loss of mechanical strength over time may be more useful in designing the composite implants of the present invention. Biodegradability of the scaffold may be a function of the implant to promote complete cycles of remodeling, wherein autologous tissue organization eventually replaces the implanted scaffold material. By doing so, the remodelable implant reduces the risk of thrombosis and intimal hyperplasia often encountered in non-biodegradable implants. A goal of the remodeling therefore is for the cell infiltration, remodeling, smooth muscle cell organization, and extra-cellular matrix formation to establish a native structure that becomes load-bearing in a time period consistent with the mechanical degradation of the degradable scaffold. In some cases, the scaffold biodegradation resulting in mechanical strength loss may primarily be the result of biofragmentation, in which the mechanical integrity of the polymer layer diminishes due to a mechanical fracturing of the layer structure. In this environment, mass loss due to biodegradation may be minor in comparison to the mechanical strength loss. In fact, the biodegradable scaffold fragments may remain integrated within the remodeled host tissue for an extended period of time without exhibiting a substantial reduction in mass, such as a reduction of less than 20% of the initial mass in a time period in which the biodegradable layer/scaffold exhibits at least 50% loss in mechanical strength. Once biofragmentation occurs, the remodeled native tissue may desirably be exposed to increased biomechanical stress, which can promote in situ cellular differentiation and tissue maturation.

The biodegradation of the polymer layers may provide the implant with an initial level of structural integrity to support the remodeling process, but a timely diminished structural integrity after a threshold period of time that is designed to be consistent with the timing of the remodeled tissue to possess the capacity to be substantially load-bearing. A targeted scaffold degradation time of between 1-12 months may preferably allow sufficient cell infiltration and remodeling while mechanical loading is transitioned to the newly formed extra-cellular matrix. In some embodiments, at least one of the biodegradable polymer layers experience loss of at least 50% of mechanical strength in no less than 30 days of continuous exposure to human blood at physiological conditions. For the purposes hereof, the term "mechanical strength" is intended to refer to tensile strength. For the purposes hereof, the term "physiological conditions" is intended to refer to the normal condition of blood in the human body, such as normal temperature, pH, oxygenation, entrained or dissolved gas concentrations, and pressure of blood. In some embodiments, each of the biodegradable polymer layers experience loss of at least 50% of mechanical strength in no less than 30 days of continuous exposure to human blood at physiological conditions. In some embodiments, at least one of the biodegradable polymer layers experience loss of at least 90% of mechanical strength in no less than 90 days of continuous exposure to human blood at physiological conditions. In some embodiments, at least one of the biodegradable polymer layers experience loss of at least 90% of mechanical strength in no less than 180 days of continuous exposure to human blood at physiological conditions. In some embodiments, each of the biodegradable polymer layers experience loss of at least 90% of mechanical strength in no less than 180 days of continuous exposure to human blood at physiological conditions.

In some embodiments, one or more of the layers of the implant, such as one or more of inner layer 14 and outer layer 18, may comprise a fiber matrix of randomly or non-randomly oriented polymer fibers. The fiber arrangements of the fiber matrices preferably provide a porosity to promote tissue ingrowth. Different layers of the implant may have different porosities, different pore sizes, and different pore size gradients, as defined by the arrangement of polymer fibers in each layer. In some embodiments, the polymer fiber matrix may be woven, non-woven, braided, aligned axially, aligned radially, random, spiral, or the like. Different layers of the implant may have different polymer fiber arrangements, and one region of a layer of the implant may have a different polymer fiber arrangement from another region of the layer. Moreover, the polymer fibers themselves may have characteristics, such as average fiber diameter, that have an impact on cell infiltration, migration, and organization. Thus, different layers of the implant may have different fibers, different average fiber diameters, and different fiber arrangements.

Figure 3:
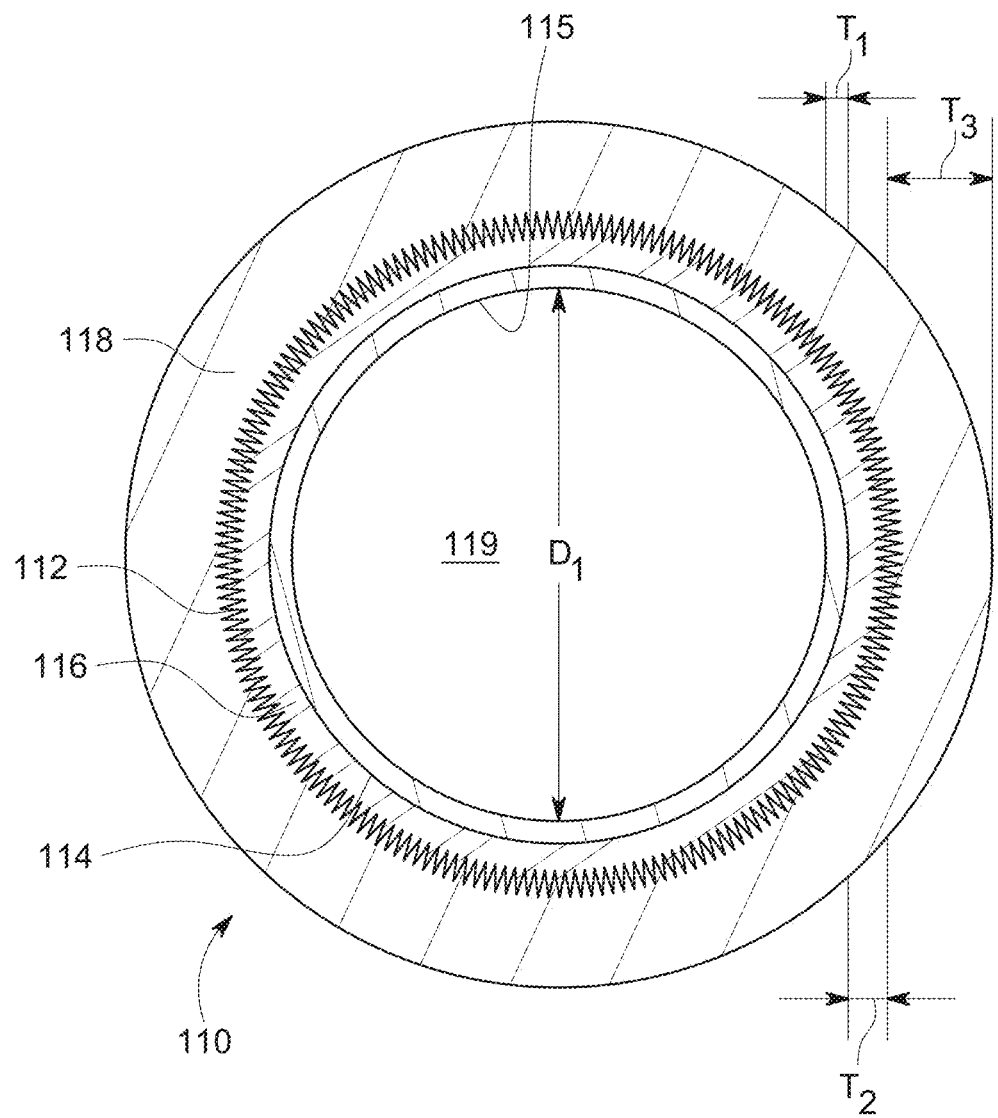
FIG. 3 is a cross-sectional schematic illustration of a composite implant of the present invention.

A cross-sectional view of a composite implant 110 of the present invention is illustrated in FIG. 3 having an inner layer 114, a second or mid layer 116, an outer layer 118 and a support 112. In some embodiments, support 112 may be embedded between second layer 116 and outer layer 118. In some embodiments, second layer 116 may be bonded to outer layer 118 with support 112 embedded therebetween. Second layer 116 may be mechanically bonded to outer layer 118 through openings in support 112. Moreover, inner layer 114 may be bonded to second layer 116.

Applicants have determined that a specific arrangement of layers, each with specific attributes can achieve a composite implant with novel functionality. In particular, a multiple layer scaffold arrangement with the layers having respectively unique constructions within critical ranges offers synergistic remodeling functionality not observed in conventional devices. The construction illustrated in FIG. 3 is an example of such a specific composite arrangement that has proven to achieve success as a remodelable construct to generate a permanent autologous tissue vessel replacement.

As illustrated in FIG. 3, inner layer 114 may be arranged to define a lumenal wall 115 of a tubular implant 110, so as to seal blood fluid within lumen 119 and to target neointimal tissue formation as part of the remodeling process. Inner layer 114 may therefore act as relatively dense but porous structure that acts as a selective barrier to erythrocyte transmural migration. In some embodiments, one aspect of the construction of inner layer 114 that has been found to be important is the size and arrangement of fibers making up the layer. Inner layer 114 may comprise a first arrangement of fibers, such as biodegradable polymer fibers. The first arrangement may be consistent throughout inner layer 114, or may be confined to a portion or region of inner layer 114. In preferred embodiments, the first arrangement may be consistent throughout inner layer 114, and includes an arrangement of fibers having an average fiber diameter of less than 1.5 µm. In some embodiments, inner layer 114 includes an arrangement of fibers having an average fiber diameter of less than 1 µm. In some embodiments, inner layer 114 includes an arrangement of fibers having an average fiber diameter of between 250 nm and 1 µm.

By forming inner layer 114 with fibers of relatively small average diameter, such as an average diameter of less than 1 µm, small inter-fiber pores are established for inner layer 114. Upon implantation and blood contact, protein adsorption may rapidly occur, initiating the process of neointimal layer formation on lumenal wall 115 of inner layer 114. The radial support provided by composite implant 110 is such that neointima can quickly form and begin to remodel via smooth muscle proliferation and circumferential organization, which is a primer for endothelial cell migration and function.

Figure 4:
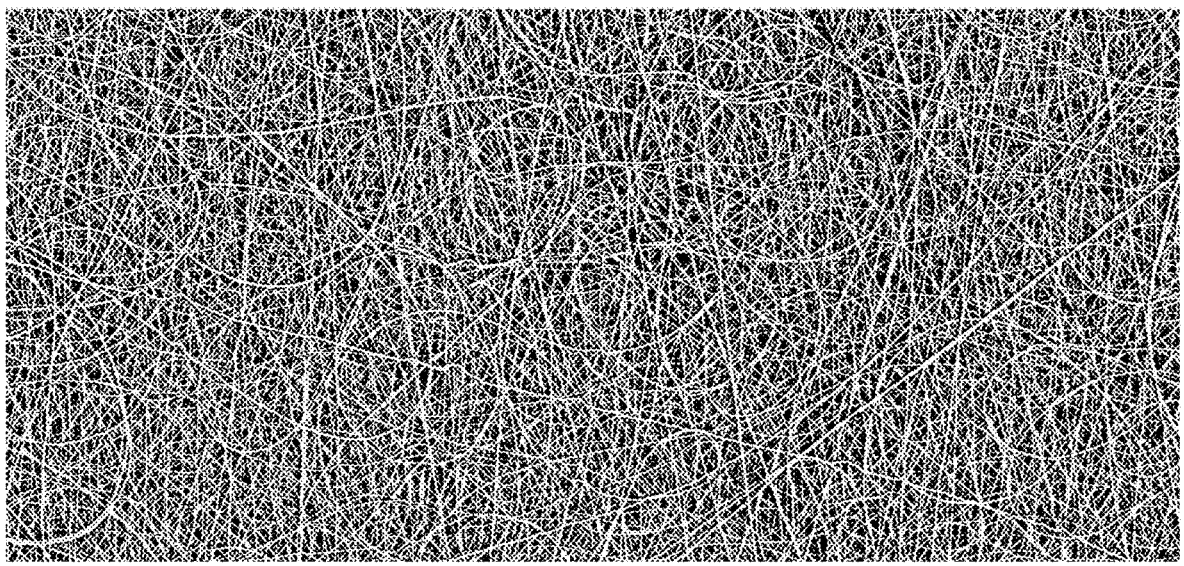
FIG. 4 is a scanning electron microscopic image of a fibrous polymeric layer of a composite implant of the present invention.

In one embodiment, the fibers making up inner layer 114 may comprise one or more biodegradable polymer materials in a non-woven arrangement. A scanning electron microscopic image of an example inner layer 114 is illustrated in FIG. 4.

In some embodiments, inner layer 114 has a thickness $T_1$ of between 1 and 200 µm. In some embodiments, inner layer 114 has a thickness $T_1$ of between 10 and 50 µm. Inner layer 114 may have a porosity configured to prevent erythrocyte transmural migration therethrough. In some embodiments, inner layer 114 may exhibit a planametric porosity of between 1-60%. In some embodiments, inner layer 114 may exhibit a planametric porosity of between 5-50%. In some embodiments, inner layer 114 may exhibit a planametric porosity of between 10-50%. In some embodiments, inner layer 114 may exhibit a planametric porosity of between 25-50%. For the purposes hereof, the term "planameteric porosity" is intended to refer to a two-dimensional void space along a cross-sectional plane of inner layer 114, such as that illustrated in the SEM of FIG. 4.

In some embodiments, inner layer 114 has an average pore size $P_1$ in an initial, non-degraded condition. In some embodiments, the average pore size $P_1$ is different than the average pore sizes of one or more of second layer 116 and outer layer 118. In one embodiment, average pore size $P_1$ is smaller than the average pore sizes of each of second layer 116 and outer layer 118. In some embodiments, the average pore size $P_1$ is substantially similar to the average pore sizes of one or more of second layer 116 and outer layer 118. Preferably, average pore size $P_1$ is effective to substantially prevent red blood cell transmission through inner layer 114.

In some embodiments, inner layer 114 may have an initial (pre-degradation) pore size gradient which permits host cell, such as macrophage, migration therein to support the remodeling process, while simultaneously preventing erythrocyte transmural migration completely therethrough.

Second layer 116 may be provided to generate transitional strength for the radial pressure load, and may operate in combination with support 112 to carry longitudinal and circumferential stress in the implant wall. By forming second layer 116 with relatively larger fibers than those of inner layer 114, such as an average diameter of greater than 1 µm, larger, dimensionally interconnected pores may be established for second layer 116. The second layer 116 may comprise a second arrangement of fibers, such as biodegradable polymer fibers. The second arrangement may be consistent throughout second layer 116, or may be confined to a portion or region of second layer 116. In preferred embodiments, the second arrangement may be consistent throughout second layer 116, and includes an arrangement of fibers having an average fiber diameter of greater than 1 µm. In some embodiments, second layer 116 includes a second arrangement of fibers having an average fiber diameter of between 1 and 20 µm. In some embodiments, second layer 116 includes a second arrangement of fibers having an average fiber diameter of between 5 and 10 µm. The average fiber diameter of the second arrangement of fibers is preferably larger than the average fiber diameter of the first arrangement of fibers in inner layer 114 in order to establish a larger pore size between fibers.

In one embodiment, the fibers making up second layer 116 may comprise one or more biodegradable polymer materials in a non-woven arrangement.

In some embodiments, second layer 116 has a thickness $T_2$ of between 25 and 500 µm. In some embodiments, second layer 116 has a thickness $T_2$ of between 50 and 500 µm. In some embodiments, second layer 116 has a thickness $T_2$ that is greater than the thickness $T_1$ of inner layer 114.

Second layer 116 may have a porosity configured to encourage host cell migration into second layer 116 to support the remodeling process. In some embodiments, second layer 116 may exhibit a planametric porosity of between 10-60%. In some embodiments, second layer 116 may exhibit a planametric porosity of between 25-50%. In some embodiments, second layer 116 may exhibit a planametric porosity that is greater than the planametric porosity of inner layer 114.

In some embodiments, second layer 116 has an average pore size $P_2$. In some embodiments, the average pore size $P_2$ of second layer 116 is different than the average pore sizes of one or more of first layer 114 and outer layer 118. In one embodiment, average pore size $P_2$ of second layer 116 is greater than the average pore size $P_1$ of inner layer 114. Average pore size $P_2$ is preferably of appropriate dimension to facilitate infiltration of immune and progenitor cells into second layer 116, as well as migration of such cells throughout second layer 116. In addition, the pores of second layer 116 are preferably three-dimensionally interconnected to promote cell signal integration and cellular remodeling of the construct.

Second layer 116 may be mechanically or otherwise bonded to inner layer 114 to an extent sufficient to resist delamination of the respective layers under typical loads imparted upon implant 110 in an initial, non-biodegraded condition.

Outer layer 118 may be provided to enclose support 112 between layers of the scaffold. In some embodiments, outer layer 118 may bond to second layer 116. The bond between outer layer 118 and second layer 116 may include mechanical bonding of the fibers. In some embodiments, support 112 may be embedded between outer layer 118 and second layer 116. Outer layer 118 may bond to second layer 116 through cells (not shown) of support 112. In some embodiments, one or both of outer layer 118 and second layer 116 may bond to support 112, at least through mechanical bonding.

Outer layer 118 may comprise a third arrangement of fibers, such as biodegradable polymer fibers. The third arrangement of fibers may be consistent throughout outer layer 118, or may be confined to a portion or region of outer layer 118. In preferred embodiments, the third arrangement may be consistent throughout outer layer 118, and includes an arrangement of fibers having an average fiber diameter of greater than 1 µm. In some embodiments, outer layer 118 includes a third arrangement of fibers having an average fiber diameter of between 1 and 20 µm. In some embodiments, outer layer 118 includes a third arrangement of fibers having an average fiber diameter of between 5 and 10 µm. The average fiber diameter of the third arrangement of fibers for outer layer 118 is preferably larger than the average fiber diameter of the first arrangement of fibers in inner layer 114.

Figure 5:
FIG. 5 is a scanning electron microscopic image of a fibrous polymeric layer of a composite implant of the present invention.

In one embodiment, the fibers making up outer layer 118 may comprise one or more biodegradable polymer materials in a non-woven arrangement. A scanning electron microscope image of an example outer layer 118 is illustrated in FIG. 5.

In some embodiments, outer layer 118 has a thickness $T_3$ of between 10 and 500 μm. In some embodiments, outer layer 118 has a thickness $T_3$ of between 10 and 300 μm. In some embodiments, outer layer 118 has a thickness $T_3$ of between 30 and 200 μm. In some embodiments, outer layer 118 has a thickness $T_3$ that is greater than the thickness $T_1$ of inner layer 114.

Outer layer 118 may exhibit a planametric porosity of between 10-60%. In some embodiments, outer layer 118 may exhibit a planametric porosity of between 25-50%. In some embodiments, outer layer 118 may exhibit a planametric porosity that is greater than the planametric porosity of inner layer 114.

Outer layer 118 has an average pore size $P_3$ that may be different than the average pore sizes of one or more of inner layer 114 and second layer 116. In one embodiment, average pore size $P_3$ of outer layer 118 is greater than the average pore size $P_1$ of inner layer 114. In some embodiments, average pore size $P_3$ may be similar to average pore size $P_2$ of second layer 116. Average pore size $P_3$ is preferably of appropriate dimension to facilitate infiltration of immune and progenitor cells into outer layer 118, as well as migration of such cells throughout outer layer 118. In addition, the pores of outer layer 118 are preferably three-dimensionally interconnected to promote cell signal integration and cellular remodeling of the construct.

The fibers making up inner, second, and outer layers 114, 116, 118, such as biodegradable polymer fibers, are preferably long and narrow, as illustrated in FIGS. 4 and 5. The fibers may be arranged into layers by various processes, including by electrospinning, as described in further detail hereinbelow. In some embodiments, the electrospinning fiber deposition process can be controlled to orient fibers as desired within a layer. For example, the fibers may be oriented randomly or non-randomly within a layer or within a region of a layer. Example non-random fiber orientations include circumferential, wherein the fibers are substantially "aligned" orthogonal to the lumenal axis, and axial, wherein the fibers are substantially aligned parallel to the lumenal axis. For the purposes hereof, the term "aligned" is intended to refer to a length axis of a fiber being generally straight along a defined direction. It is to be understood that the length axis of a fiber may not be a straight line, but rather extends generally along a direction that can be recognized. It is further to be understood that "aligned" fibers may include some portion of fibers that are non-aligned or non-parallel with one another. Instead, the "aligned" fibers mean that the majority of fibers in a set of aligned fibers are generally parallel with one another. In some embodiments, "aligned" fibers means that at least 80% of fibers in a set of aligned fibers are generally parallel with one another. In some embodiments, "aligned" fibers means that at least 90% of fibers in a set of aligned fibers are generally parallel with one another.

Figure 6:
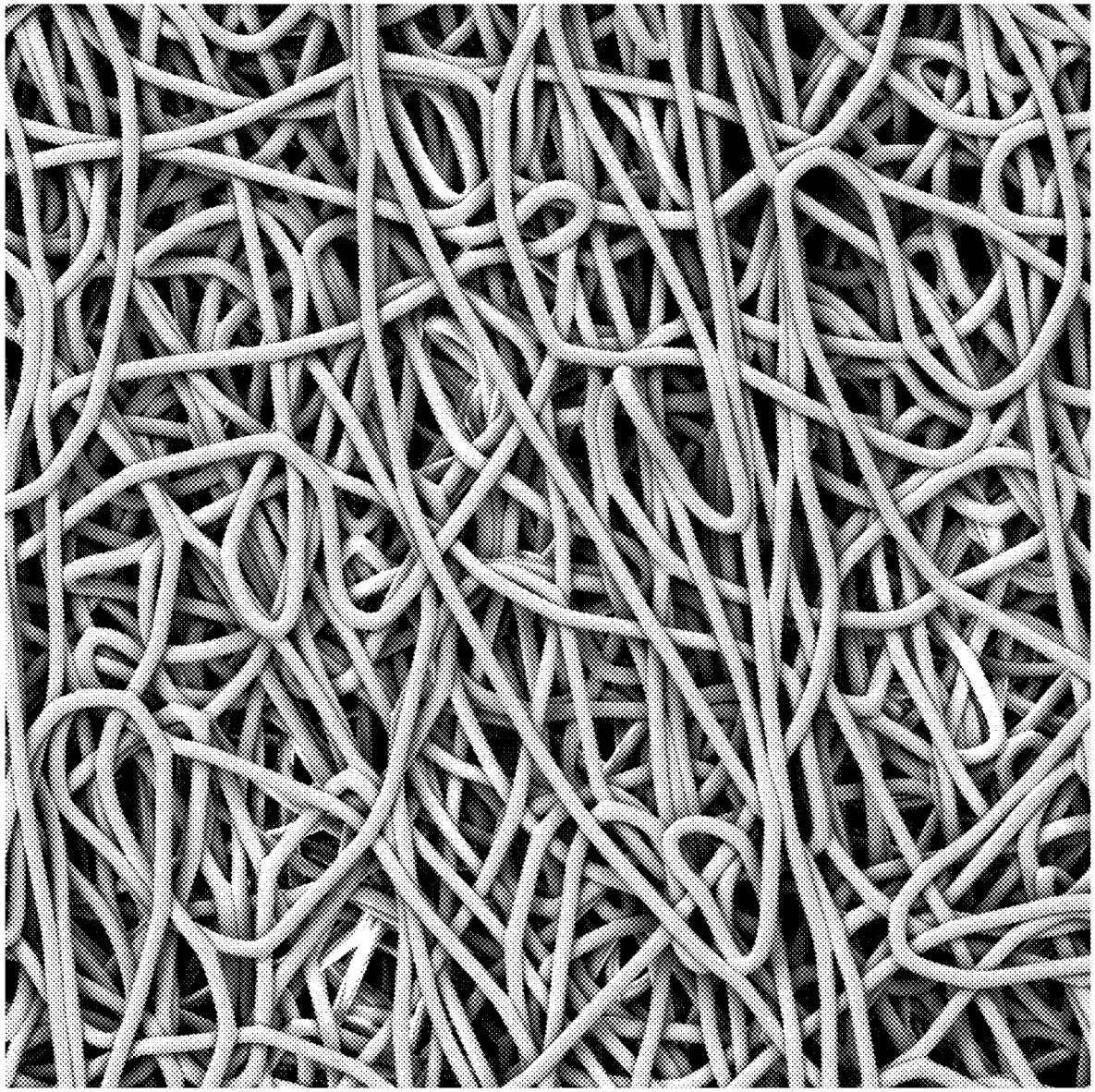
FIG. 6 is a scanning electron microscopic image of a fibrous polymeric layer of a composite implant of the present invention with the polymeric fibers oriented randomly.
Figure 7:
FIG. 7 is a scanning electron microscopic image of a fibrous polymeric layer of a composite implant of the present invention with the polymeric fibers oriented in axial alignment.

In some embodiments of the present invention, fibers of one or more layers of composite implant 110 may be randomly oriented, as shown in FIG. 6. The random orientation may be in woven or non-woven fiber arrangements. In some embodiments, the random orientation of fibers is in non-woven arrangements. In one embodiment, the first non-woven arrangement of biodegradable polymer fibers of inner layer 114 is randomly oriented, and at least one of the second and third non-woven arrangements of biodegradable polymer fibers of the respective second and outer layers 116, 118 are one of: (i) aligned substantially parallel with the lumenal axis, or (ii) aligned substantially orthogonal to the lumenal axis. An example axially-aligned fiber layer is illustrated in the image of FIG. 7. Each of the second and third non-woven arrangements of biodegradable polymer fibers may be one of: (i) aligned substantially parallel with the lumenal axis, or (ii) aligned substantially orthogonal to the lumenal axis. In other embodiments each of the first, second, and third non-woven arrangements of biodegradable polymer fibers may be randomly oriented.

Fiber orientation may be directed to impart certain physical properties to composite implant 110. For example, oriented fibers can provide strength characteristics in the form of tensile strength and resistance to elongation along directions parallel to their length axes. Radial or circumferential orientation/alignment can resist aneurism or even over expansion under arterial pressures. Certain fiber orientation alignments can aid implant flexibility, such as in directions normal to fiber orientation. Additionally, fiber orientation alignment combinations may improve suture retention strength. Applicants contemplate various fiber orientation alignment combinations in order to achieve desired implant physical properties.

It is an aspect of the implants of the present invention to be useful as remodeled autologous tissue vessels having relatively small lumenal diameters. In some embodiments, lumenal diameter $D_1$ may be less than 10 mm. In some embodiments, lumenal diameter $D_1$ may be less than 6 mm. In some embodiments, lumenal diameter $D_1$ may be between 1-6 mm. It is to be understood that lumenal diameter $D_1$ may fluctuate primarily depending upon changing internal fluid pressures, but may also be in equal along the lumenal axis. Lumenal diameter $D_1$ may also change as implant 110 is remodeled. For the purposes hereof, the composite implants of the present invention are contemplated to be useful as constructs for the replacement of, for example, small-diameter native vessels, such as those having a lumenal diameter of about 6 mm or less.

Resilient Support

With reference back to FIGS. 1 and 2, implant 10 includes resilient support 12, which has minimal resistance to deformation under external mechanical stimulus, yet helps generate flexure stability in combination with the polymer scaffold. In this regard, resilient support 12 is considered "radially compliant". It is believed that factors in proper remodeling may involve an appropriate cyclic stretch of smooth muscle cells and to upregulate vascular endothelial growth factor (VEGF) expression. A further consideration is the influence of tensile stress/strain on the structure and organization of smooth muscle cells during development and remodeling, particularly as to the orientation of such cells. These considerations may be addressed through thus use of resilient support 12 that exhibits radial compliance within a certain tolerance. For the purposes hereof, the term "compliance" is intended to refer to the ratio of the diameter change of a structure as it expands in the radial direction in response to a given change in pressure applied to that structure. In this case, the structure is resilient support 12. Compliance may be reported as percentage change in the internal diameter of the structure per a 100 mm Hg change in pressure applied to an inner surface of a tubular support 12.

In some embodiments, resilient support 12 exhibits a compliance of between 1% and 50%/100 mm Hg. In some embodiments, resilient support 12 exhibits a compliance of between 5% and 50%/100 mm Hg.

Radially resilient support 12 may be manufactured from any biocompatible material that possesses the ability to be shaped into a tubular structure having the desired compliance. Polymeric fibers may be employed, such as polyurethanes, polyethylene terephthalate, polypropylene, polytetrafluoroethylene, and the like. Polymeric fibers making up resilient support 12 may preferably be elastomeric polymers such as polyurethane elastomers or composite fibers that act in an elastic manner. In some embodiments, metals such as stainless steel and cobalt-chromium alloys are useful in the manufacture of support 12. Shape memory alloys such as Nitinol may be used as well. Shape memory elements or filaments may be made of one or more shape memory alloys, and may be coated with one or more polymers for biocompatibility.

Figure 8:
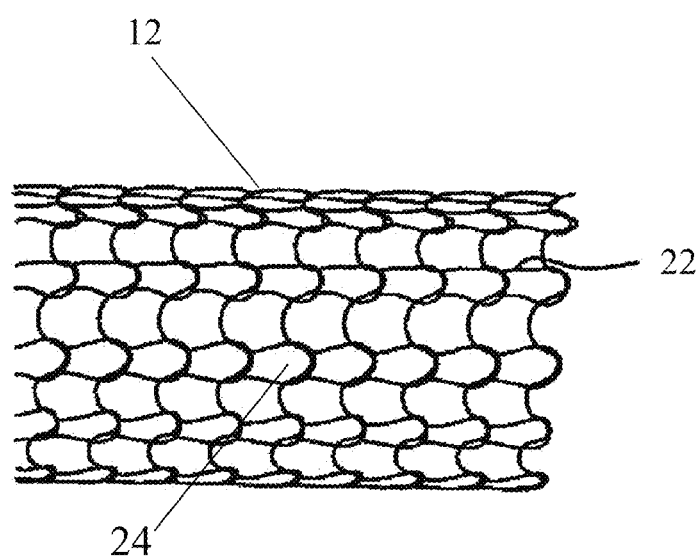
FIG. 8 is a schematic illustration of a tubular resilient support element of a composite implant of the present invention.
Figure 9:
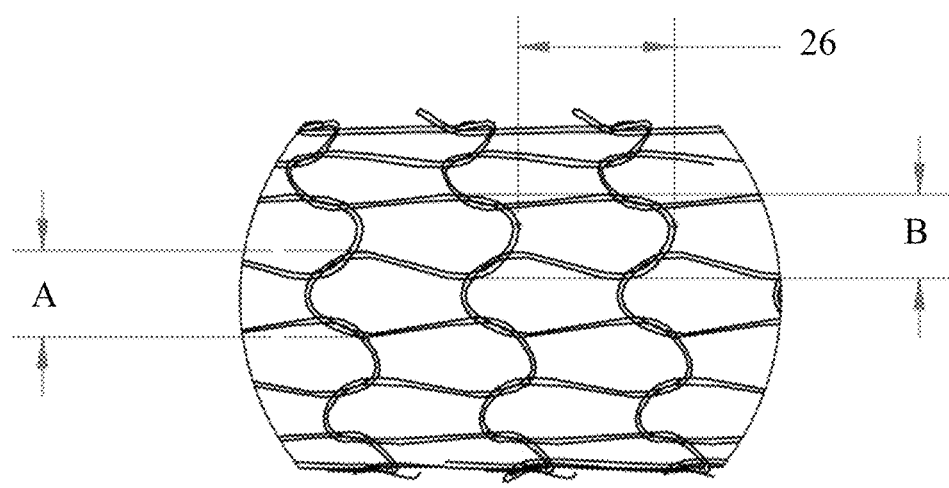
FIG. 9 is an enlarged schematic illustration of a portion of a tubular resilient support element of a composite implant of the present invention.

An embodiment of a tubular resilient support 12 is illustrated in FIGS. 8 and 9, wherein support 12 is formed of one or more elements 22 that are preferably knitted, woven, laser cut, or braided into a generally tubular structure. In the illustrated embodiment, support 12 may comprise a circular weft knitted structure that may be used to permanently limit long term dilation and aneurysm risk of the remodeling vessel. The knit of support 12 may be designed with cells 24 having interstitial dimensions that provide the primary radial support of the underlying one or more polymer layers and overall scaffold mechanical continuity. In the illustrated embodiment, cells 24 of support 12 have a dimensional relationship of width "A" divided by width "B" (A/B) of between 0.8 and 1.2. In some embodiments, the dimensional relationship of A/B may be between 0.9 and 1.1, and may preferably be about 1.

In the knit embodiment of FIG. 9, support 12 may include between 5 and 20 wales per circumference. In some embodiments, support 12 may include between 7 and 15 wales per circumference. In some embodiments, support 12 may include between 8 and 12 wales per circumference. In some embodiments, support 12 includes 10 wales per circumference. In some embodiments, cells 24 of support 12 may have a course height 26 of between 0.5-5 mm. In some embodiments, cells 24 of support 12 may have a course height 26 of between 1-2.5 mm. In some embodiments, cells 24 of support 12 may have a course height 26 of between 1.2-2 mm.

Support 12 may, in some embodiments, be knitted from metal wire, such as stainless steel or Nitinol alloy. Metal wires ranging in diameter from 25 to 150 µm may be useful for support 12 of the present invention. In some embodiments, desired radial compliance and tubular dimensional properties may result from knitting support 12 in a manner providing cells 24 that alternate in the circumferential direction between larger and smaller cells 24. Closed ends of cells 24 may be either rounded or generally square-shaped or variations in between, and the sides of each cell 24 may turn outward, be parallel, or turn inward. However, other geometries for cells 24 are contemplated as being useful in support 12 of the present invention.

Micropatterning

The composite implant of the present invention is preferably arranged to provide synergistic performance characteristics not available with the individual layered components. Thus, as a composite, operational challenges such as delamination, aneurysm formation, premature fragmentation, and uncontrolled mechanical strength degradation can be overcome. Each polymer layer of the scaffold may comprise a fibrous network of preferably nonwoven biodegradable fibers, which are generally entangled, but have limited bonding between overlapping and adjacent fibers. The unconstrained degrees of freedom facilitated by the lack of intra-layer fiber bonding permits individual fibers to move relative to other fibers. On a macroscopic scale, this freedom of relative fiber movement imparts flexibility to the implant by allowing individual fiber rotation and translation when under load.

In order to improve uniformity and macroscopic flexure characteristics of the composite implant, one or more layers may individually or in combination be subjected to processing to obtain a micropattern of a plurality of axially spaced apart circumferential recesses defining respective hinge regions at which at least one of the respective layers are more flexible than non-hinge regions thereof. The hinge regions may also coordinate to provide increased flexibility, defined by a reduced resistance to flexure under an applied force, to the implant as a whole.

Figure 10:
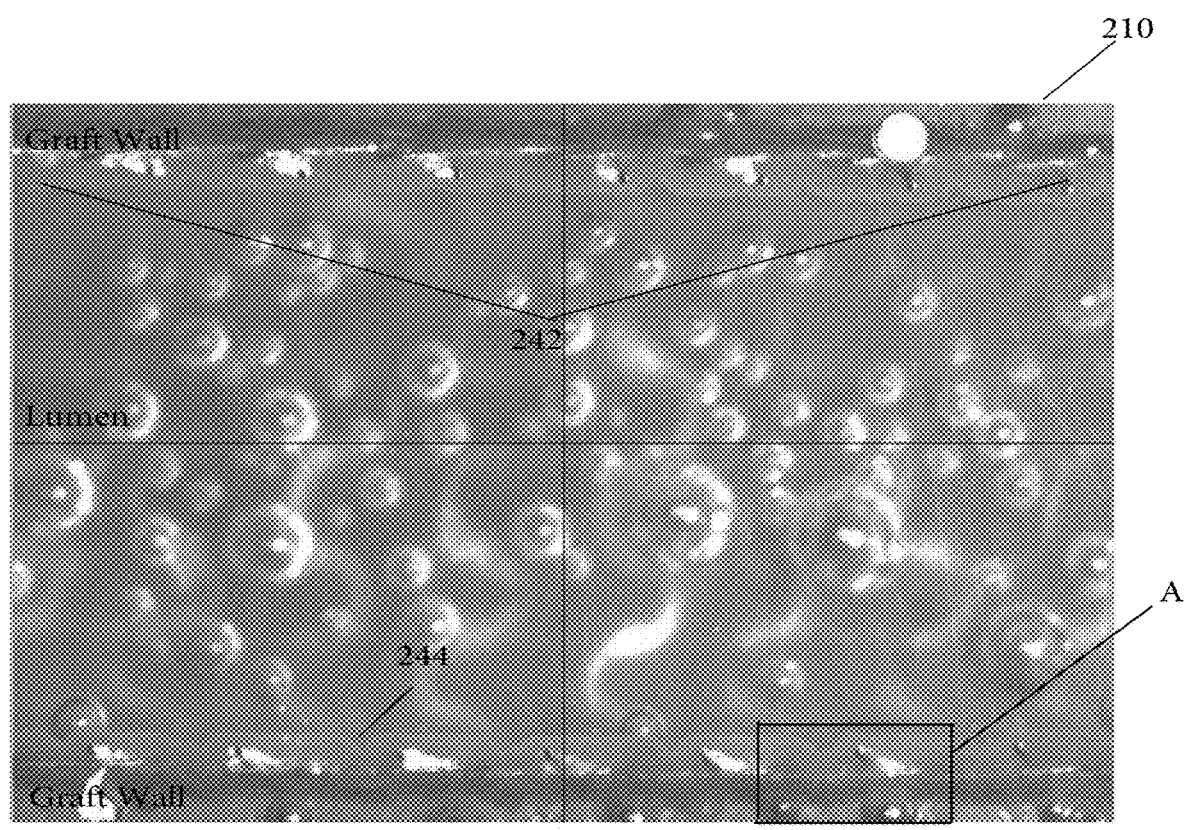
FIG. 10 is an image of a micropatterned composite implant of the present invention.
Figure 11:
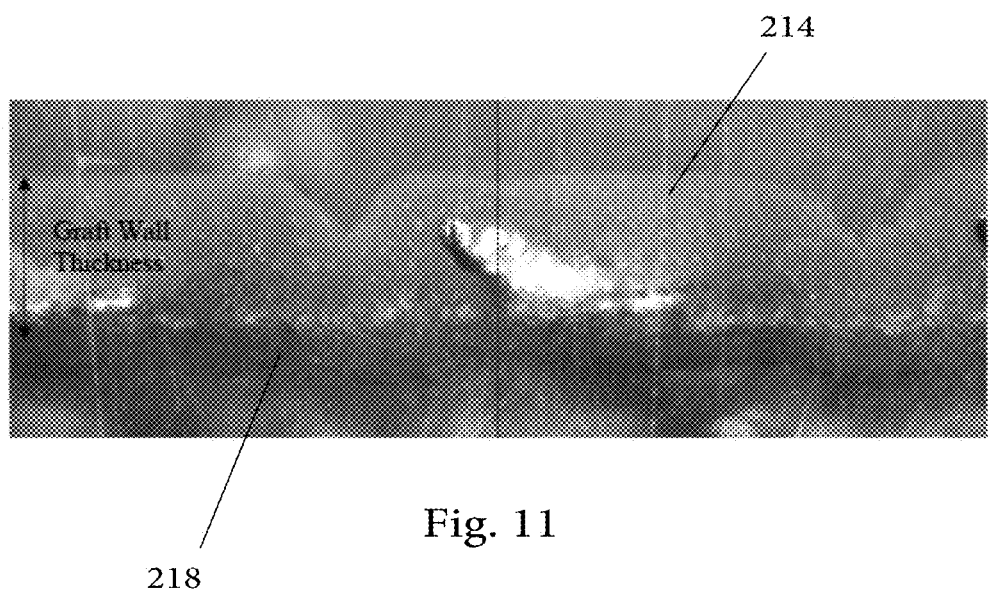
FIG. 11 is an enlarged image of a portion of the micropatterned composite implant illustrated in FIG. 10.
Figure 12:
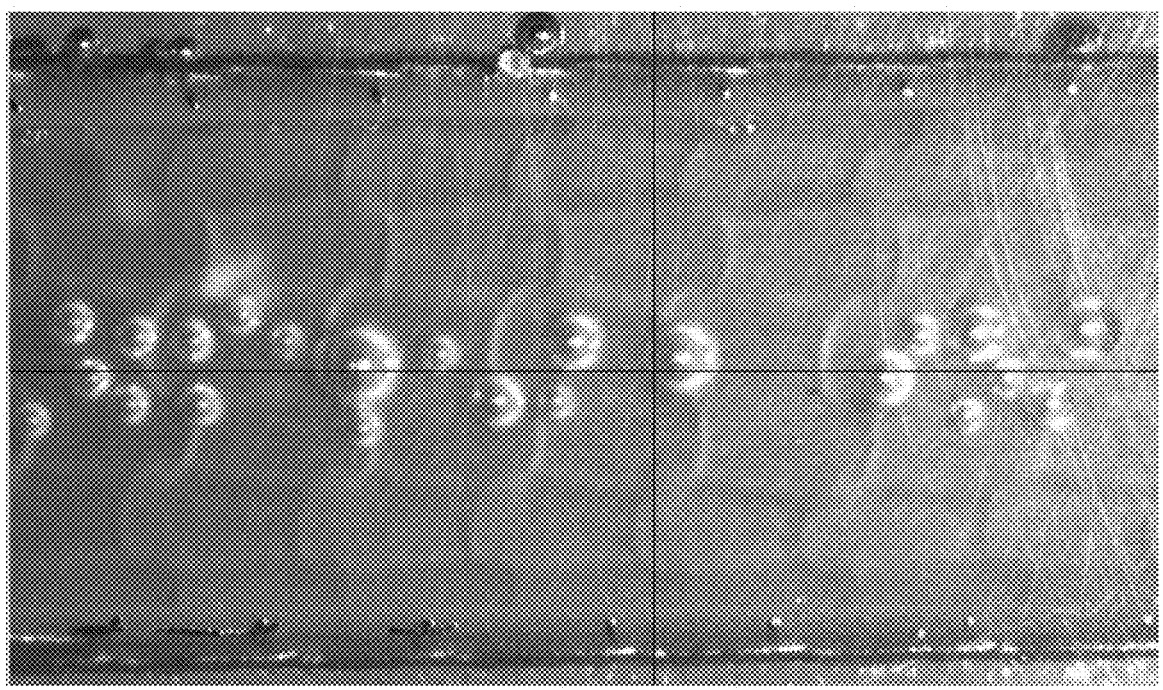
FIG. 12 is an image of a non-micropatterned composite implant of the present invention.

A sectioned view of a composite implant 210 with a micropattern 242 of axially spaced-apart circumferential recesses 244 is illustrated in the image of FIG. 10. An enlarged view of region "A" in FIG. 10 is shown in the image of FIG. 11. The images of FIGS. 10 and 11 show a segment of a micropatterned composite implant 210 that was embedded in epoxy, cured, and precision ground to attain a hemi-section of the tubular composite implant 210. The surface was then polished prior to imaging. Artifact air-bubbles are apparent in the images. A non-micropatterned example composite implant is shown in the segmented image of FIG. 12 for comparison purposes.

Recesses 244 of micropattern 242 may be defined by regions of one or more of inner layer 214, support 212, and outer layer 218 that are deflected and otherwise permanently shaped by processing to deviate from a substantially cylindrical configuration, such as at unshaped regions 246. In some embodiments, therefore, micropattern 242 may be formed without addition of material to, or removal of material from, composite implant 210. Instead, micropattern 242 comprises shaped regions of composite implant 210.

Figure 13:
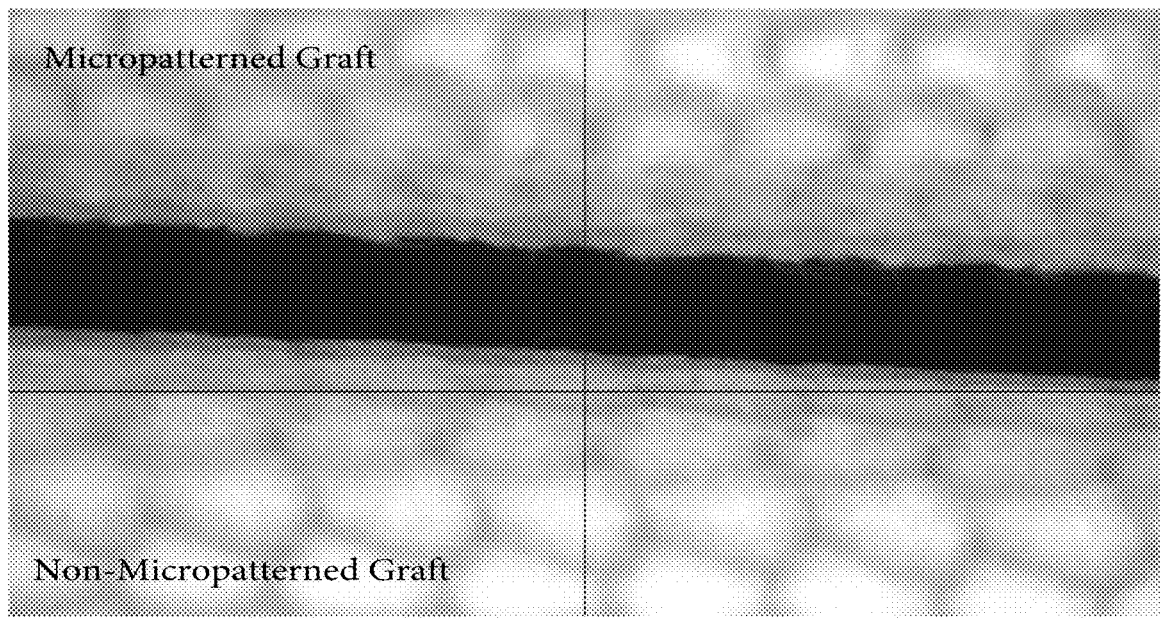
FIG. 13 is an image of a comparison of the outer surfaces of micropatterned and non-micropatterned composite implants of the present invention.
Figure 14:
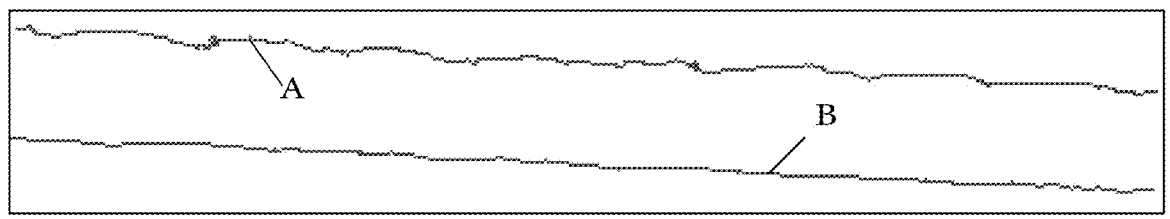
FIG. 14 represents traced outer surface edges of the outer surfaces illustrated in FIG. 13.

FIG. 13 demonstrates a comparison of outer surfaces of a micropatterned composite implant 210 (top) to the outer surface of a non-micropatterned composite implant (bottom). FIG. 14 represents the traced outer surface edges of the compared micropatterned implant outer surface (A) and non-micropatterned implant outer surface (B). Texturing in the micropatterned composite implant demonstrates polymer fiber conformance to the support underlying support structure, where overlapping wires protrude and then regress, creating a textured surface. This effect is pronounced as a result of the micropatterning process.

Figure 15:
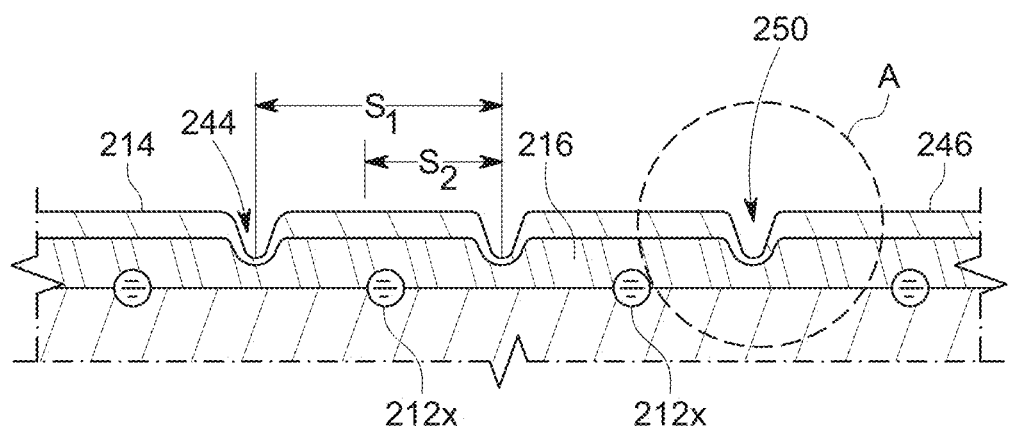
FIG. 15 is a schematic cross-sectional view of a composite implant of the present invention.

To better illustrate the arrangement of recesses 244, FIG. 15 schematically depicts an enlarged cross-sectional view as imaged in FIG. 11. Each of inner layer 214, second layer 216, and outer layer 218 remain present at recess 244, although the respective layer thicknesses $T_1$, $T_2$, and $T_3$ of one or more of the layers may be somewhat compressed from that described above with respect to composite implant 110. In some embodiments, a thickness of at least one of inner layer 214, second layer 216, and outer layer 218 may be compressed by at least 10% at one or more of recesses 244. In some embodiments, a thickness of at least one of inner layer 214, second layer 216, and outer layer 218 is compressed by at least 30% at one or more of recesses 244. In some embodiments, a thickness of at least one of inner layer 214, second layer 216, and outer layer 218 is compressed by at least 50% at one or more of recesses 244. For the purposes hereof, the term "compressed" is intended to refer to a reduction in layer thickness ($T_1$, $T_2$, $T_3$) as compared to the respective layer thicknesses at unshaped regions 246.

As shown in FIG. 15, composite implant 210 may include second layer 216 between inner layer 214 and outer layer 218, and particularly between inner layer 214 and support 212. Mechanical bonding between second layer 216 and outer layer 218 through cells 224 of support 212 may be enhanced at recesses 244, wherein a higher percentage of fibers of second layer 216 are mechanically bonded to fibers of outer layer 218 at recesses 244 than such bonding at unshaped regions 246. The mechanical bonding limits mobility relative to adjacent fibers to thereby focus flexibility to respective annular hinge regions 250 of recesses 244. A thickness $T_2$ of second layer 216 may be compressed at one or more of recesses 244, and may be compressed by at least 10%, at least 30%, or at least 50%. Inner layer 214, second layer 216, and outer layer 218 may be compressed by different extents at one or more of recesses 244, including one or more of inner layer 214, second layer 216, and outer layer 218 not being compressed at one or more of recesses 244.

Figure 16:
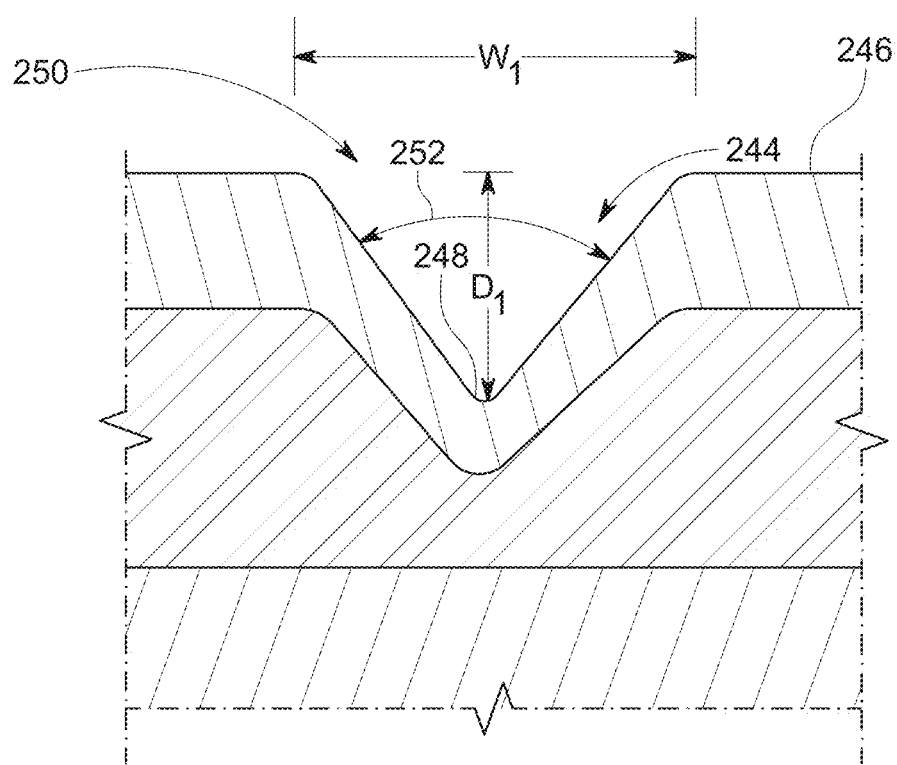
FIG. 16 is an enlarged schematic cross-sectional view of a portion of the composite implant illustrated in FIG. 15.

One embodiment of hinge region 250 is illustrated in FIG. 16 as an enlarged cross-sectional view of area "A" shown in FIG. 15. In this embodiment, recess 244 is shown deflected from unshaped region 246 to form a vertex 248 at which flexing of the layers forming recess 244 is focused. Vertex 248 may be a relatively defined crease or fold, or may instead be an arcuate or pseudo-arcuate region of recess 244. As a result, vertex 248 may not be limited to a point, a series of points, or a line along recess 244, and may instead include a region of recess 244 at which flexure is focused.

In some embodiments, recess 244 forms an internal angle 252 that defines the two sides forming vertex 248. In some embodiments, internal angle 252 may be between 10° and 170°. In some embodiment, internal angle 252 may be between 30° and 150°. In some embodiment, internal angle 252 may be between 60° and 120°.

Recesses 244 of micropattern 242 may be axially spaced apart by a spacing dimension $S_1$, which is a dimension between vertices 248 of adjacent recesses 244. Spacing dimension $S_1$ may be uniform throughout micropattern 242, or may instead be different at different regions of micropattern 242. In some embodiments, a pattern of different spacing dimensions $S_1$ may be employed to provide desired flexibility characteristics to implant 210. In some embodiments, different spacing dimensions $S_1$ may be used without a specific pattern. Spacing dimension $S_1$ may typically be between 0-10 mm. In some embodiments, spacing dimension $S_1$ may be between 0.1-5 mm. In some embodiments, spacing dimension $S_1$ may be between 0.5-3 mm.

A second spacing dimension $S_2$ is illustrated in FIG. 15 as the dimension between a vertex 248 of recess 244 and an adjacent circumferential wire 212x of support 212. The cross-sectional view of FIG. 15 illustrates the relative positioning of circumferential wires 212x and recesses 244 of micropattern 242. In particular, hinge regions 250, which define points of flexure, may be positioned between adjacent circumferential wires 212x of support 212.

Recesses 244 may be provided with various depth dimensions $D_1$ and width dimensions $W_1$ that provide the desired physical properties for the composite implant. In some embodiments, depth dimension $D_1$ may be between 0.001-1 mm. In some embodiments, depth dimension $D_1$ may be between 0.01-0.5 mm. In some embodiments, depth dimension $D_1$ may be between 0.05 and 0.3 mm. In some embodiments, width dimension $W_1$ may be between 0.001-1 mm. In some embodiments, width dimension $W_1$ may be between 0.01-0.5 mm.

Figure 17:
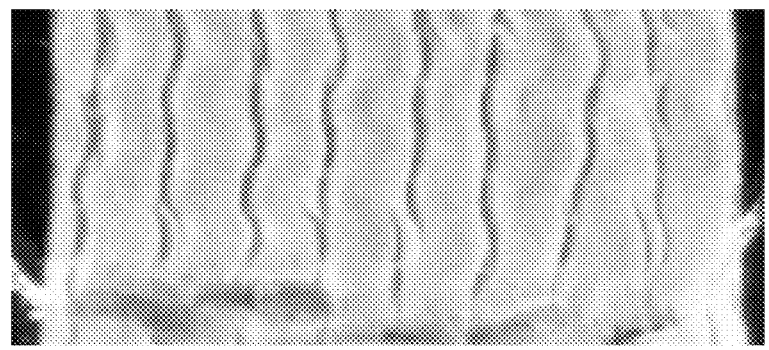
FIG. 17 is an image of a composite implant of the present invention with micropatterning.

An image of an example micropattern in a composite implant of the invention is shown in FIG. 17.

It is also contemplated that some circumferential recesses of the micropatterns may be oriented substantially perpendicularly with respect to the lumenal axis, while other circumferential recesses of the described micropatterns may be oriented non-perpendicularly with respect to the lumenal axis.

In the illustrated embodiment, recesses 244 extend radially outwardly from lumenal axis 21. However, it is to be understood that one or more of recesses 244 may extend radially inwardly toward lumenal axis 21. In some embodiments, micropattern 242 includes some recesses 244 extending radially outwardly and some recesses 244 extending radially inwardly.

Electrospinning

The composite implants of the present invention may be manufactured using an electrospinning process utilizing a voltage field between a nozzle and a collector to create fibers from a polymer solution. The voltage of each of the nozzle and the collector can influence how the fiber is produced. In some embodiments, to control fiber deposition, the nozzle voltage may be controlled between 5 kV and 20 kV, and the collector voltage controlled between −1 kV and −10 kV. Electrospun polymer fiber constructs are well known in the art, and it is contemplated that those of ordinary skill in the art are equipped to manufacture the polymer fiber layers described herein through such known electrospinning techniques.

EXAMPLES

The following examples set forth materials and methods for constructing example embodiments of the composite implants of the present invention. The examples described herein, however, should not be considered limiting in any way as to the materials, construction, or methods of construction of the composite implants of the present invention.

Example 1—Tubular Graft

A Nitinol wire was circular weft knit over a 4.0 mm stainless steel mandrel. The knit was uniformly formed around the mandrel such that the cell spacing ratio was approximately 1. The Nitinol was knit in a pattern creating a tubular structure with a course height of approximately 1.5 mm and 10 wales per inch. After knitting was complete, the Nitinol was heat set and a series of steps that impart corrosion resistance was performed.

Figure 18:
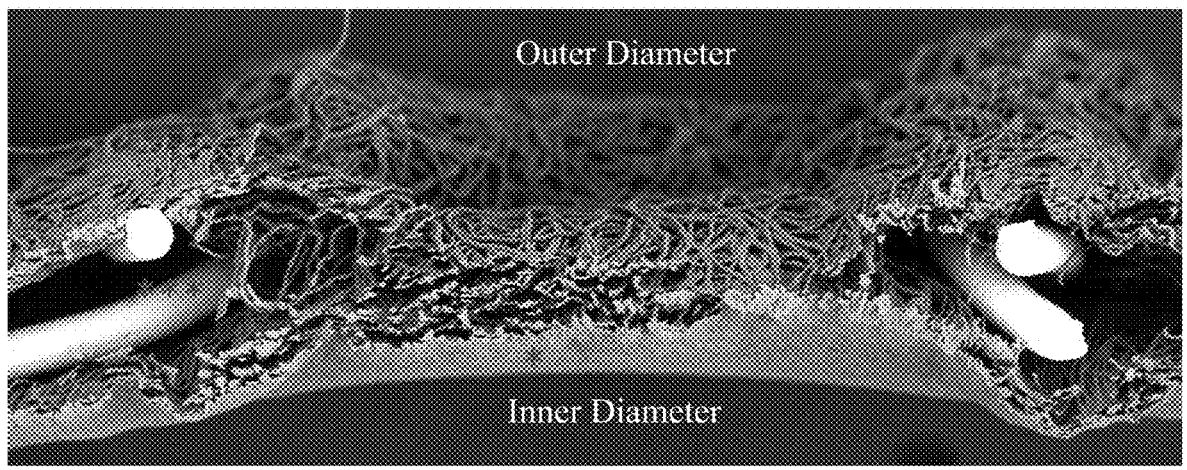
FIG. 18 is a scanning electron microscopic image of a cross-section of a composite implant of the present invention.

Two PLGA polymer solutions were prepared with a blend ratio of PLA:PGA of at least 80:20, with the compositions ranging from 5-20 wt. % polymer in solution. Upon dissolution, the solutions were transferred to a syringe and loaded into an electrospinning machine. A 4.0 mm stainless steel mandrel was loaded in the electrospinning machine and rotated. A first PLGA solution was loaded into a syringe pump and extruded through the needle tip. The needle tip-to-collector distance was set, and a constant voltage difference was applied between the needle tip and the rotating mandrel collector. From selected settings, an initial layer of uniform fibers of less than 1 μm diameter were deposited on the mandrel until a wall thickness of approximately 10-25 μm was achieved. A second PLGA solution was loaded into the electrospinning machine, and the settings adjusted so that a second layer was deposited with fibers having a diameter of approximately 1-10 μm until a layer thickness of approximately 100-200 μm was created. The finished Nitinol support was then deployed over the top of the second polymer layer. A final polymer layer was deposited on top of the Nitinol, encapsulating it within the polymer network, as shown in FIG. 18.

Tubular grafts were measured and cut to approximately 18 cm in length, placed in a polytetrafluoroethylene (PTFE) tube, and packaged in a gas permeable pouch prior to sterilization. Samples were sterilized with biological indicators using ethylene oxide gas, followed by off-gassing for at least 72 hours prior to testing.

In-vitro performance testing of the sample devices was completed to evaluate the mechanical properties of these grafts according to ISO 7198. All box plots of test results depicted herein show the calculated mean with a dotted line and the median as the middle solid line.

Figure 19:
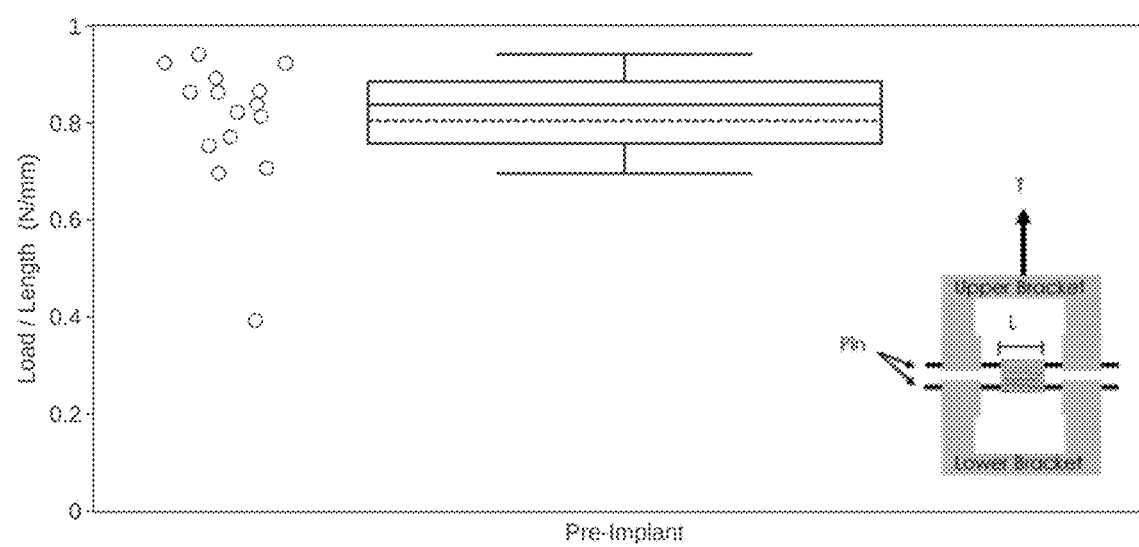
FIG. 19 is a box plot of circumferential tensile test results for testing composite implants of the present invention. The insert image depicts the test setup where the lower bracket is fixed in place and the upper bracket is extended at 50 mm/min. Two pins are placed inside the sample and clamped in each bracket prior to the start of each test.

Circumferential and longitudinal tensile testing of the composite device was completed using a force testing system (LS Starrett, MA). To evaluate the circumferential strength, and approximately 5 mm segment of the graft tube was cut and placed in a test fixture. The sample was extended at a rate of 50 mm/min until failure of the sample was captured. The calculated maximum load per sample length was then calculated as $T_{max}/2*L$ as shown in FIG. 19. The calculated mean of the 15 samples was 0.8 N/mm.

Figure 20:
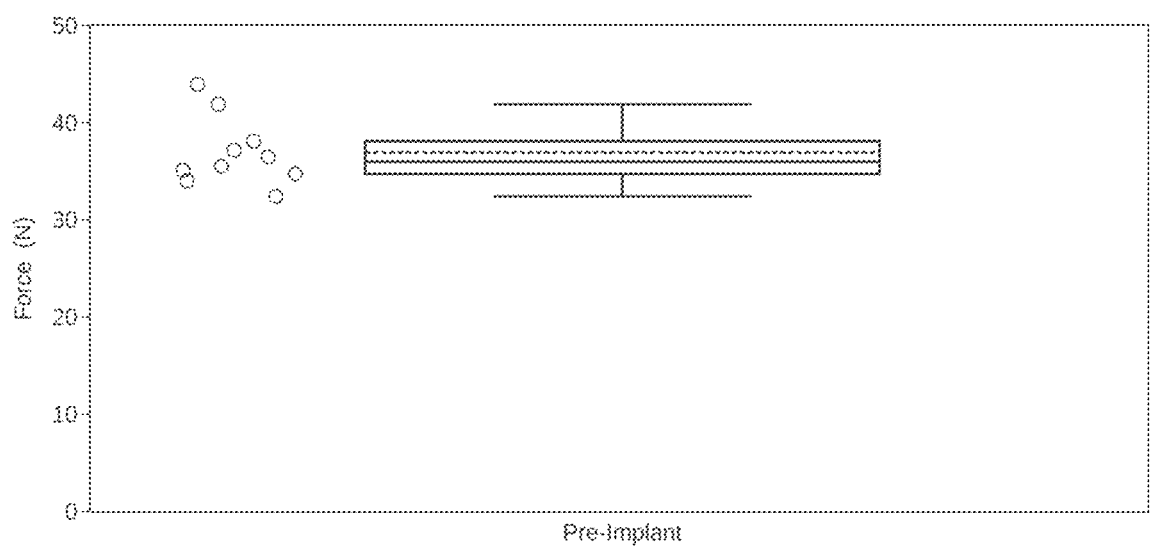
FIG. 20 is a box plot of longitudinal tensile test results for testing composite implants of the present invention.

Longitudinal tensile tests were completed with 10 cylindrical graft samples, each approximately 70 mm in length. Each sample end was positioned with a clamp-to-clamp distance of 50 mm, and the upper bracket was extended at 50 mm/min while a load cell measured the resulting force. The maximum force was recorded and the calculated mean was 36.9 N, as shown in FIG. 20.

Figure 21:
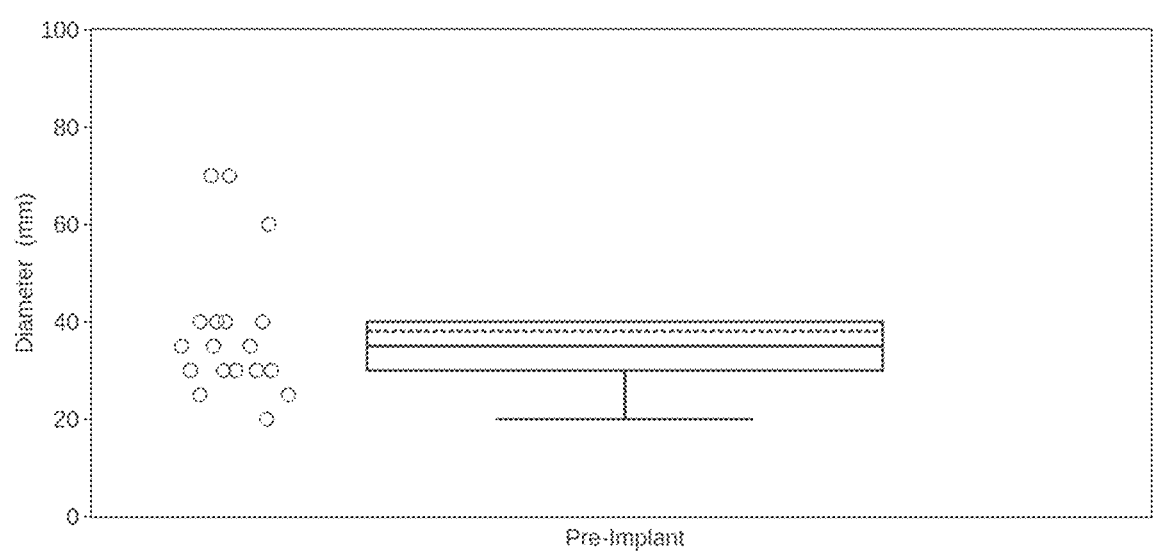
FIG. 21 is a box plot of flexibility testing of composite implants of the present invention.

To evaluate flexibility, 18 devices were coiled around a stepped cone of decreasing diameter. Each step of the cone consisted of a 5 mm diameter change. The stepped fixture tested the length of the graft under bending stress. The smallest diameter that the graft was able to flex around without buckling was recorded. The calculated mean diameter was 38 mm, as shown in FIG. 21.

Figure 22:
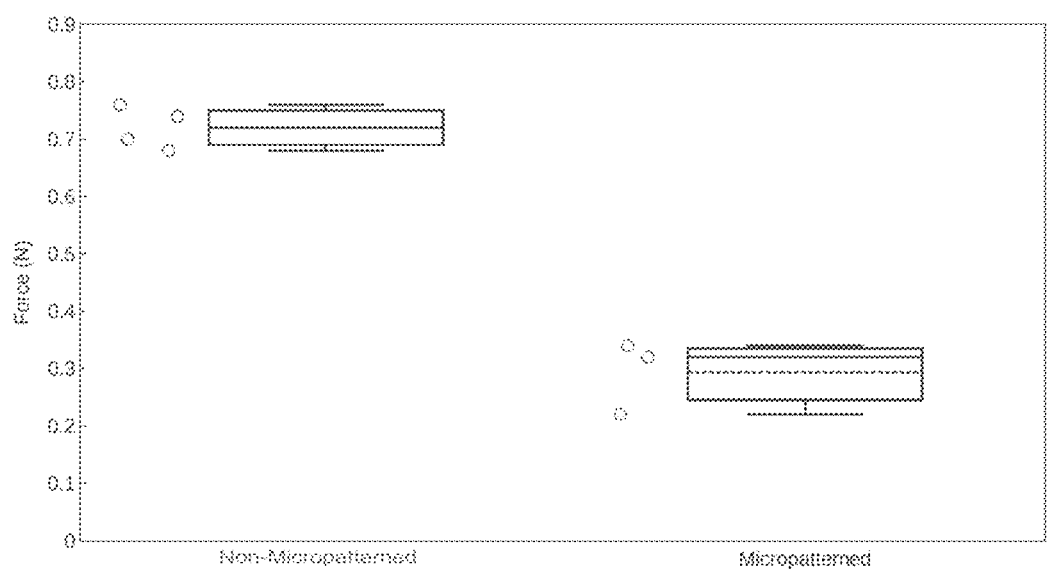
FIG. 22 is a box plot of flexibility testing of composite implants of the present invention.
Figure 23:
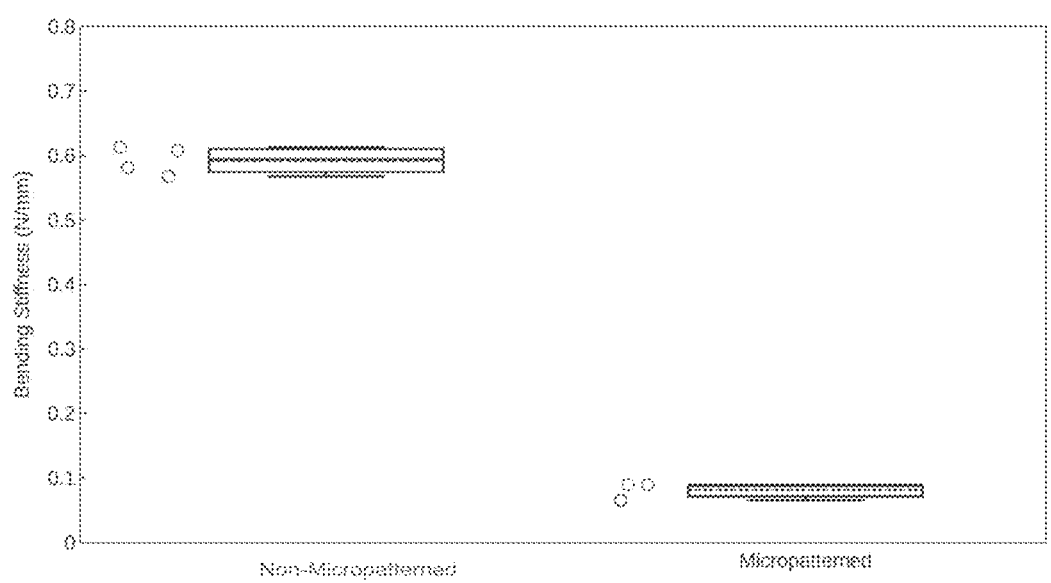
FIG. 23 is a box plot of flexibility testing of composite implants of the present invention.
Figure 24:
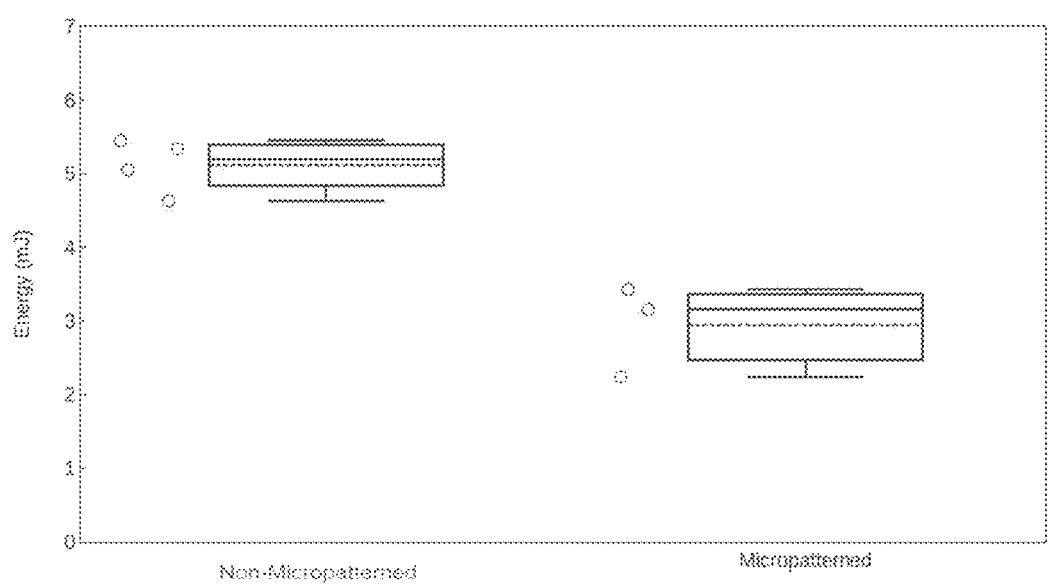
FIG. 24 is a box plot of flexibility testing of composite implants of the present invention.

In vitro performance testing of finished devices was completed to evaluate the flexural properties of the grafts according to ISO 7198 as well. Three-point flexure tests of non-micropatterned (smooth) and micropatterned composite implants were completed. To evaluate the flexural mechanics, approximately 50 mm long segments of the implantable tube were cut and placed in a test fixture supporting the ends spaced 40 mm apart. The center of the device sample was extended at a rate of 50 mm/min with a 10 mm round cylinder until a 15 mm displacement was achieved. The maximum force during the displacement was captured (FIG. 22) and total energy during the test was calculated (FIG. 24). The slope of the force-displacement curve during the first 1 mm of displacement was used to compare the initial bending stiffness (FIG. 23).

These flexure tests indicated that the micropatterned devices reduced the maximum flexure force by approximately 59%, the initial bending stiffness by 86%, and total energy required to flex the device through 15 mm of displacement by 43%.

Figure 25:
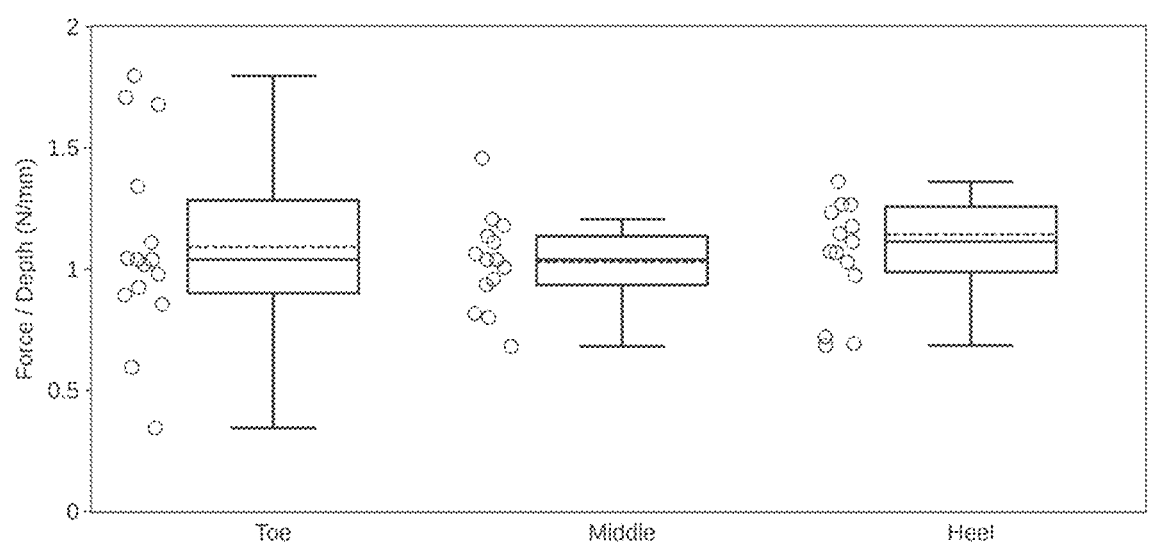
FIG. 25 is a box plot showing maximum suture retention force divided by the depth that the suture was placed from the cut edge.

To evaluate suture retention strength, the end of a 45 mm graft sample was cut at an oblique angle and three 6-0 suture hoops were placed approximately 1 mm inside the cut edge at 90° apart (toe, middle, heel). The other end of the sample was clamped and fixed in the lower bracket while the suture was pulled at 50 mm/min. The maximum force was recorded and normalized by the depth that the suture was placed from the cut edge. The calculated mean across all 15 samples was 1.09 N for toe, 1.03 N for middle, and 1.14 N for heel, as shown in FIG. 25.

Figure 26:
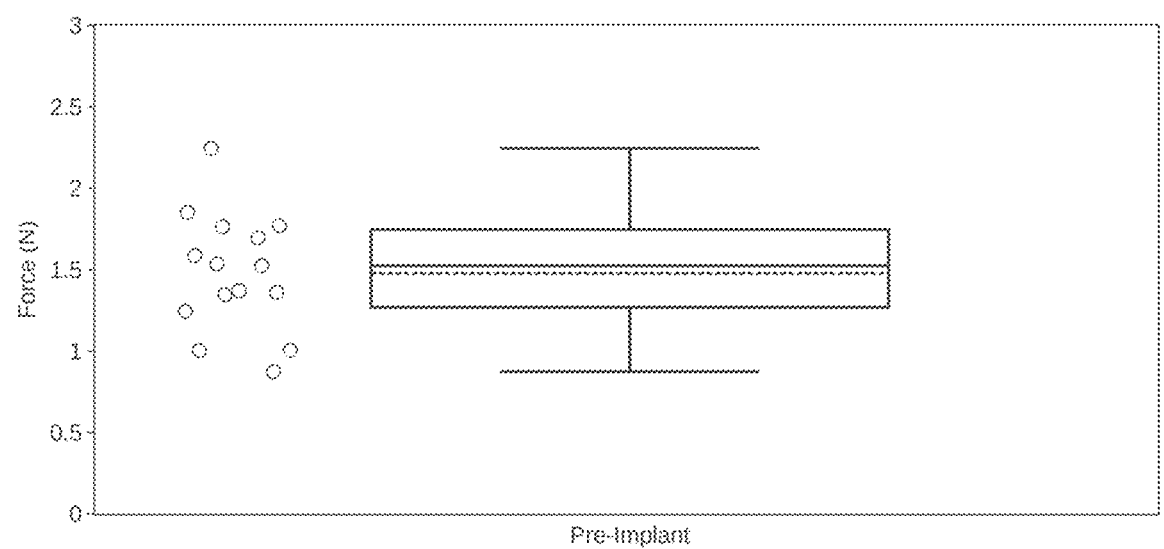
FIG. 26 is a box plot of force to initiate delamination of composite implants of the present invention.

A delamination test was developed to evaluate the bonding strength between the outer layer and the second layer. To prepare samples, grafts of 50 mm in length were sectioned and the cylinder was cut longitudinally to create flat samples 50×12.6 mm. On one end, the outer layer and support were physically separated from the underlying layers, thereby creating two tabs each approximately 15 mm long. Each tab was then clamped in the force tester and the upper tab was pulled at 20 mm/min while measuring the force. The peak force required to initiate delamination was captured and recorded for the 15 samples. The mean force to initiate delamination was 1.48 N, as shown in FIG. 26.

Figure 27:
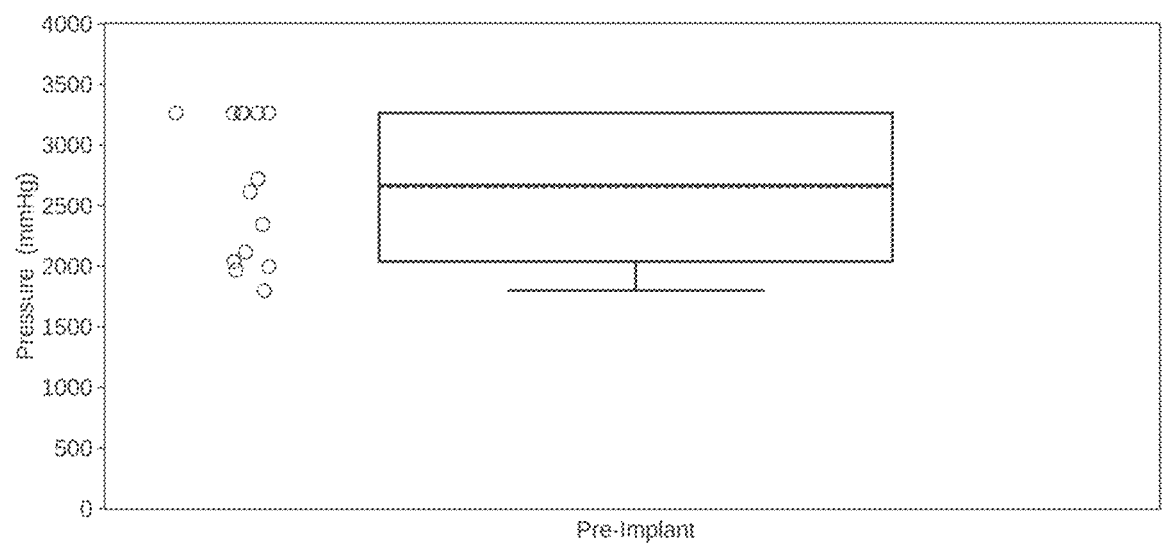
FIG. 27 is a box plot of maximum burst pressure of composite implants of the present invention.

A burst test was developed to characterize how much internal pressure the device can hold without rupturing. For this test, fresh heparinized ovine blood was acquired and the activated clotting time was measured using a Hemochron microcoagulation test system. The blood clotting time was then adjusted to a therapeutic level of 400-500 seconds using protamine sulfate and heparin sulfate as needed. Graft samples were cut to 50 mm lengths and placed in-line with a syringe pump (Chemyx Inc., TX) with the outflow end capped after de-aeration. A pressure transducer was placed in-line with the syringe pump to measure changing pressure. The syringe pump was then set to displace a blood-filled syringe plunger at approximately 80 mL/min to pressurize the sample. Pressure curves were acquired for 15 samples, and the maximum pressure prior to rupture was captured. It was found that the maximum transducer pressure was 3264 mm Hg, which limited capturing the actual burst pressure of 6 samples. For these samples, the maximum pressure was recorded as the maximum sensor value of 3264 mm Hg. The mean maximum pressure across all samples was 2656 mm Hg, as shown in FIG. 27.

Example 2—Ovine Preclinical Implant

Tubular scaffold conduits were prepared as set forth in Example 1.

Figure 28:
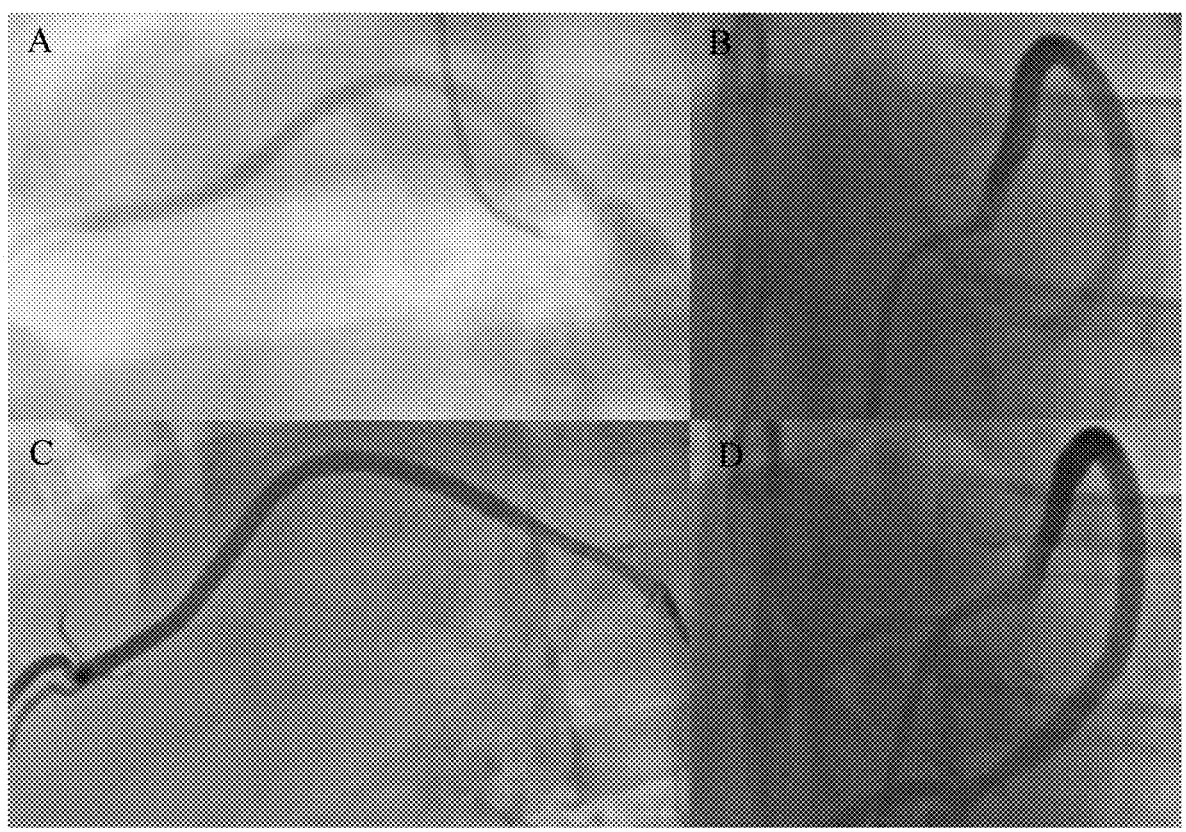
FIG. 28 depicts a representative sequence of an ovine implant cine angiogram followed up at 0 days (A), 46 days (B), 93 days (C), and 178 days (D), with respect to an implanted composite implant of the present invention.

Implants were completed as a standard on-pump CABG procedure. Study protocols for each animal indicated a left thoracotomy followed by cannulation and initiation of extracorporeal circulation. After cardioplegic induced cardiac arrest, an arteriotomy was created on the distal target artery, typically the left anterior descending (LAD), and the test graft was anastomosed in an end-to-side fashion using a continuous 7-0 polypropylene suture. The proximal end of the test graft was then similarly anastomosed to an arteriotomy made in the descending aorta with a continuous 6-0 polypropylene suture. A permanent occlusion was made in proximal LAD by ligation with a polyester tie resulting in the distal coronary bed being perfused solely by the test graft. They were then weaned from extracorporeal circulation. Following implant surgery, the animals were recovered and survived to approximately 90 or 180 days. Cine angiography was completed at 0, 45, 90, and 180 days for patency as shown in one representative implant follow-up sequence, illustrated in FIG. 28.

Example 3—Ovine Preclinical Explant

Figure 29:
FIG. 29 depicts a radiograph image of an explanted composite implant of the present invention.

After surviving 90 days, the heart and graft tissues were resected en bloc, perfusion rinsed with saline, and then perfusion fixed with 10% neutral buffered formalin (NBF). The device was then trimmed, removed from the heart, and digitally radiographed to evaluate integrity of the Nitinol support structure as seen in FIG. 29.

The device was then further trimmed and then sectioned to remove the mid-level for scanning electron microscopy imaging. The remaining tissue was embedded in Spurr resin, and the resulting blocks were sectioned and stained with Hematoxylin and Eosin (H&E).

Figure 30A:
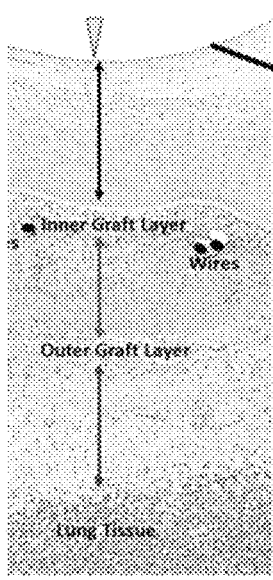
FIG. 30A illustrates a Hematoxylin and Eosin (H&E) stained mid-section showing remodeling of an explanted composite implant of the present invention at 90 days post-implantation.
Figure 30B:
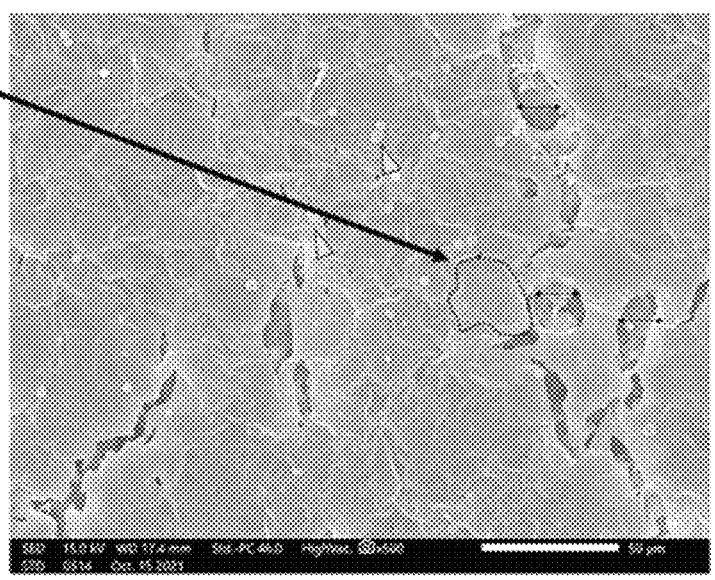
FIG. 30B is a scanning electron microscopic image of the region illustrated in FIG. 30A.
Figure 31A:
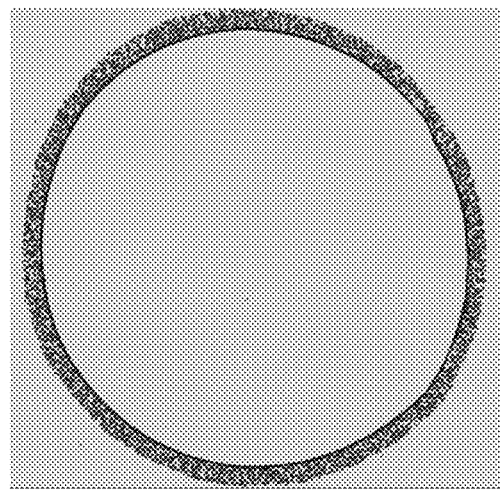
FIGS. 31A and 31B represent explanted graft samples analyzed with Visiopharm software, with FIG. 31A representing a non-implanted and support-free implant, and FIG. 31B representing a 90-day explant Movat's Pentachrome (MP)-stained section.
Figure 31B:
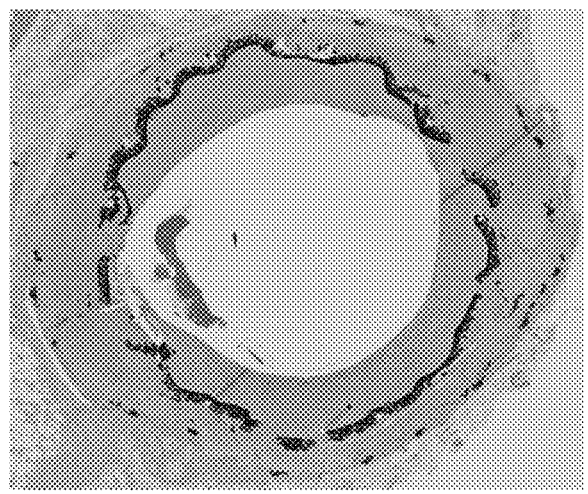

Explant data from this ovine animal bypass graft indicated accelerated remodeling of the polymer scaffold. As depicted in FIGS. 30A and 30B, this animal explant showed excellent cell migration into the scaffold. The graft had neovascularized collagenous adventitial extra-cellular matrix, mild inflammatory response by host immune cells, and significant lumenal remodeling within the 90 days of implant. The top double arrow in FIG. 30A indicates maturing neointima with endothelium at the lumenal surface. The middle double arrow in FIG. 30A indicates remodeling medial layer, and the bottom double arrow demonstrates infiltrated scaffold and remodeling of the periadventitial layer. The image shows confluent endothelium, as outlined on the annotated image of FIG. 30B by a dashed line, and processing artifact cracks shown by double arrows on the SEM image. Additional histologic sections further indicated that mechanical integrity of the polymer scaffold was diminishing as depicted in the before and after images of FIGS. 31A and 31B.

Using Movat's Pentachrome (MP) stained slides, histo-morphometric analysis was completed on the graft explant at three distinct cross-sections along the length of the device, approximately 2-3 cm apart, to estimate the amount of polymer degradation. At each level, the area of residual polymer graft material was quantified and then compared against naïve (de novo) and Nitinol-free samples. Results indicated that the polymer was actively degrading. The inner layer had reduced by approximately 16% by mass, and the second layer combined with the outer layer had reduced by approximately 0.4% relative to the non-implanted reference samples.

The invention claimed is:

1. A composite implant forming a tubular vascular graft defining a lumenal axis, the composite implant comprising:
   a resilient tubular support exhibiting radial compliance with respect to the lumenal axis, and being disposed circumaxially between an inner layer and an outer layer, the inner layer forming a lumenal wall of the implant and comprising a first non-woven arrangement of biodegradable polymer fibers, the outer layer forming an exterior wall of the implant and comprising a second non-woven arrangement of biodegradable polymer fibers, the first non-woven arrangement of biodegradable polymer fibers of the inner layer forming a plurality of axially spaced apart circumferential recesses defining respective hinge regions at which a first radial layer thickness of the inner layer is less than a second radial thickness of the inner layer at non-hinge regions thereof, wherein the axially spaced apart circumferential recesses extend radially outwardly from the lumenal axis toward respective vertices, and wherein each such circumferential recess forms an internal angle of between 10-170° opening from the respective vertex toward the lumenal axis.

2. The composite implant as in claim 1, including a second layer positioned adjacent to the inner layer and comprising a third non-woven arrangement of biodegradable polymer fibers with the second layer between the inner layer and the outer layer, and the resilient tubular support defining openings between adjacent spaced apart elements.

3. The composite implant as in claim 2 wherein the inner layer has a first thickness of between 1-200 μm, the second layer has a second thickness of between 50-500 μm, and the outer layer has a third thickness of between 10-300 μm.

4. The composite implant as in claim 3 wherein each of the inner layer, the second layer, and the outer layer have a planametric porosity of between 25-50%.

5. The composite implant as in claim 4 wherein the biodegradable polymer fibers include at least one of polylactic acid, polyglycolic acid, copolymers of polylactic acid and polyglycolic acid, poly(glycerol sebacate), degradable polyurethanes, polycaprolactone, polyethylene glycol, polydioxanone, elastin-like polymers, copolymers with trimethylene carbonate, and derivatives and copolymers thereof.

6. The composite implant as in claim 5 wherein the first non-woven arrangement of biodegradable polymer fibers is random, and at least one of the second and third non-woven arrangements of biodegradable fibers are one of: (i) aligned substantially parallel with the lumenal axis; or (ii) aligned substantially orthogonal to the lumenal axis.

7. The composite implant as in claim 6 wherein both of the second and third non-woven arrangements of biodegradable polymer fibers have the same alignment, being one of: (i) aligned substantially parallel with the lumenal axis; or (ii) aligned substantially orthogonal to the lumenal axis.

8. The composite implant as in claim 6 wherein each of the first, second, and third non-woven arrangements of biodegradable polymer fibers is random.

9. The composite implant as in claim 3 wherein the resilient tubular support exhibits a radial compliance of between 5% and 50%/100 mm Hg to promote smooth muscle cell organization as a component of cellular remodeling of the composite implant into a vessel of autologous tissue reinforced by the resilient tubular support.

10. The composite implant as in claim 9 wherein the resilient tubular support includes a circular weft knit of the elements.

11. The composite implant as in claim 10 wherein the inner layer forms the lumenal along a lumenal axis, and wherein the lumen has a diameter of less than 6 mm.

12. The composite implant as in claim 2 wherein the resilient tubular support is disposed between the second layer and the outer layer, and the second layer is mechanically bonded to the outer layer through the openings.

13. The composite implant as in claim 2 wherein each of the inner layer, the second layer, and the outer layer experience loss of at least 50% of tensile strength in no less than 30 days of continuous exposure to human blood at normal physiological conditions.

14. The composite implant as in claim 1 wherein the internal angle is between 60-120°, and the axially spaced apart circumferential recesses have a depth of between 0.05 and 3 mm.

15. The composite implant as in claim 14 wherein the exterior wall of the implant is free from circumferential recesses.

16. The composite implant as in claim 1 wherein the circumferential recesses are axially spaced apart by the non-hinge regions.

* * * * *

UNITED STATES PATENT AND TRADEMARK OFFICE
CERTIFICATE OF CORRECTION

PATENT NO. : 12,127,928 B2  
APPLICATION NO. : 18/531315  
DATED : October 29, 2024  
INVENTOR(S) : Chaid D. Schwarz et al.

Page 1 of 1

It is certified that error appears in the above-identified patent and that said Letters Patent is hereby corrected as shown below:

In the Claims

Column 26, Line 42, "inner layer forms the lumenal along a lumenal axis, and" should read -- inner layer forms a lumen along the lumenal axis, and --.

Signed and Sealed this  
Thirty-first Day of December, 2024

Derrick Brent  
*Acting Director of the United States Patent and Trademark Office*